United States Patent
Dias et al.

(10) Patent No.: US 10,184,027 B2
(45) Date of Patent: Jan. 22, 2019

(54) REDUCTION SENSITIVE BIODEGRADABLE POLYESTERAMIDES

(71) Applicant: DSM IP Assets B.V., Heerlen (NL)

(72) Inventors: Aylvin Jorge Angelo Athanasius Dias, Echt (NL); Zhiyuan Zhong, Echt (NL); Huanli Sun, Echt (NL); Wei Wang, Echt (NL); Fenghua Meng, Echt (NL); Jan Feijen, Echt (NL)

(73) Assignee: DSM IP ASSETS, B.V., Heerlen (NL)

( * ) Notice: Subject to any disclaimer, the term of this patent is extended or adjusted under 35 U.S.C. 154(b) by 0 days.

(21) Appl. No.: 15/502,215

(22) PCT Filed: Aug. 10, 2015

(86) PCT No.: PCT/EP2015/068365
§ 371 (c)(1),
(2) Date: Feb. 7, 2017

(87) PCT Pub. No.: WO2016/020545
PCT Pub. Date: Feb. 11, 2016

(65) Prior Publication Data
US 2017/0233527 A1 Aug. 17, 2017

(30) Foreign Application Priority Data

Aug. 8, 2014 (CN) ........................ 2014 1 0387485
Sep. 17, 2014 (EP) ..................................... 14185201

(51) Int. Cl.
C08G 69/44 (2006.01)
A61K 9/51 (2006.01)
A61K 9/50 (2006.01)
A61K 45/06 (2006.01)
C08G 75/14 (2006.01)

(52) U.S. Cl.
CPC .............. *C08G 69/44* (2013.01); *A61K 9/50* (2013.01); *A61K 9/5146* (2013.01); *A61K 45/06* (2013.01); *C08G 75/14* (2013.01); *C08G 2230/00* (2013.01)

(58) Field of Classification Search
None
See application file for complete search history.

(56) References Cited

U.S. PATENT DOCUMENTS 9,951,183 B2 * 4/2018 Dias ....................... C08G 69/44
2003/0144373 A1 7/2003 Bowman et al.
2003/0236371 A1 12/2003 Wilson et al.
2007/0134332 A1 * 6/2007 Turnell ................ A61K 9/1075
424/486
2007/0155926 A1 7/2007 Matyjaszewski et al.
2009/0171455 A1 * 7/2009 Benco ..................... A61L 31/04
623/1.49

FOREIGN PATENT DOCUMENTS

WO        200218477       3/2002
WO        2008048298      4/2008
WO        2009088912      7/2009
WO    WO 2009/088912  *  7/2009  ............. A61L 31/06

OTHER PUBLICATIONS

Biomater. Sci., 2013, vol. 1, pp. 633-646 (Year: 2013).*
Meng, F, et al., "Reduction-sensitive polymers and bioconjugates for biomedical applications", Biomaterials, Elsevier Science Publishers BV., Barking, GB., vol. 30, No. 12, Apr. 1, 2009 (Apr. 1, 2009).
Kobayashi, et al., "Synthesis of New Linear Polymers containing Thiocarbonyl Groups: Polyaddition of Dicarbothioic Acid to Diolefins," Polymer Journal, Society of Polymer Science, (1994), pp. 49-59.
Kobayashi, et al.,"Kinetics of the Addition Reactions of Thiobenzoic Acids to Styrenes or Ethynlybenzenes as the Model of Polyaddition. Study on the Rate-Determining Step and Substituent Effect." Polmyer Journal, Society of Polymer Science, (1993) pp. 507-520.
Marvel, et al., "Polythiolesters", Journal of the American Chemical Society, (1951), pp. 1100-1102.
Kai Guo, et al., "Biodegradable and injectable paclitaxel-loaded poly(ester amide) s microspheres: Fabrication and characterization", Journal of Biomedical Materials Research Part B: Applied Biomaterials, vol. 89B, No. 2, May 1, 2009 (May 1, 2009), pp. 491-500.
WO2016/020545 Search Report dated Feb. 11, 2016.
WO2007/028612 International Search Report, dated Mar. 11, 2008.

* cited by examiner

*Primary Examiner* — Brian Gulledge
(74) *Attorney, Agent, or Firm* — Kevin M. Bull

(57) ABSTRACT

The present invention relates to biodegradable polyesteramides (PEAs) comprising hydrophobic alpha-amino acids, diols, aliphatic dicarboxylic acids and optionally diamines whereby at least one of the dicarboxylic acids, diols or diamines comprises disulphide linkages. The present invention also relates to the use of the polyesteramides in medical applications such as cancer treatment, ophthalmic applications, therapeutic cardiovascular applications, veterinary applications, pain management applications, MSK applications and vaccine delivery compositions. The present invention also relates to a drug delivery composition comprising the PEA's and to a drug delivery system such as micro- or nanoparticles, micelles, liposomes, polymerosomes, micro- and nanogels, polymerosomes or nanotubes.

19 Claims, 10 Drawing Sheets

REDUCTION SENSITIVE BIODEGRADABLE POLYESTERAMIDES

Figure 1:
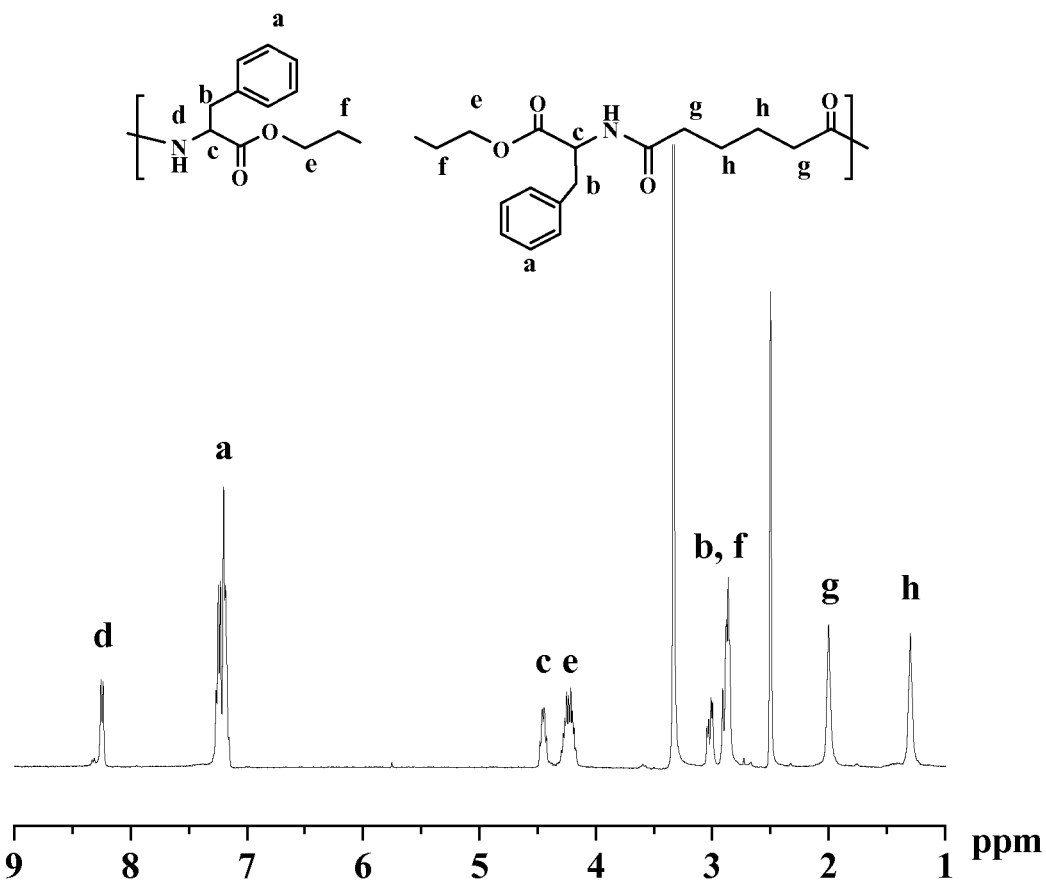

This application is a US National Phase application of International Application No. PCT/EP2015/068365, filed 10 Aug. 2015, which designated the US and claims priority to Chinese Application No. 201410387485.4, filed 8 Aug. 2014, and European application number 14185201.2, filed 17 Sep. 2014, the entire contents of each of which are hereby incorporated by reference.

The present invention relates to new reduction sensitive biodegradable polyesteramides. The present invention also relates to drug delivery compositions comprising the reduction sensitive biodegradable polyesteramides. The invention further relates to drug delivery compositions for intracellular delivery of bioactive agents.

Recently there has been growing interest in biodegradable polymers for intracellular and triggered delivery of small molecule drugs and biologics (DNA, RNA and therapeutic peptides and proteins). For intracellular delivery typically a more reductive environment is required since the intracellular environment (cell cytoplasm) is a more reductive environment than the extracellular environment.

The use of biodegradable polymers for intracellular drug delivery is known in the art. Biomaterials 30 (2009) 2180-2198, F. Meng, W. E. Hennink, Z. Zhong discloses reduction sensitive biodegradable polymers which comprise disulphide bonds as the reductive group. The disulphide bonds can be incorporated in the main or side chain of the polymer. The polymers are reported in the form of micelles, polymerosomes, micro- and nanogels but also as polymerosomes or nanotubes especially for the delivery of bioactive agents.

A disadvantage is however that the biodegradable polymers are hydrolytically degradable which makes them unstable in extracellular fluids. There is thus a high risk of premature degradation of the biodegradable polymer and consequently drug release even before the biodegradable polymers gets to the target site for triggered release. This means that higher dosages of drugs are required. A disadvantage of higher doses of drugs and their release in sites other than the targeted side may cause side effects.

Lu et. al in Polymer degradation and Stability 92, (2012) 661 reported on the use of cysteine for the preparation of polyesterurethane ureas. These materials however suffer from two major draw backs. Firstly one of the building blocks being hexamethylene diisocyanate degrades into amines which are non-natural compounds. Secondly the synthesis of polyesterurethane ureas involves the use of toxic catalysts which are not tolerated for medical applications. Moreover any incomplete degradation is observed in a reductive environment which means that some polymer fragments will remain as persistent degradation products.

Hong et al reported on the poly-amino-esters obtained by a Michael addition of disulphide bearing acrylates with N-methylethylene diamine. These polymers were difficult to control in terms of Mw due to side reactions at temperatures above 40 deg C.

Langer et. al. (J. Am. Chem. Soc 2006, 128, 39), 1279 synthesized Poly(β-amino esters) by Michael type reaction of 2 (pyridyl dithio)ethylene amine with various diacrylate monomers. These polymers were able to strongly bind to DNA to form a DNA polymer complex of 100 nm. However incomplete decomplexation was observed in a reductive environment due to the presence of tertiary amine groups that maintain their binding affinity of DNA. As a result the complex exhibited low transfection efficiency.

In many cases where reduction sensitive polymers have been made also non-degradable building blocks (other than the disulphide groups) are involved. Examples of such polymers are polyethyleneimine, polyacrylate or polyacrylamides. The non-degradable fragments present a challenge to the adoption of this technology in clinical practice since the Mw of the fragments have to be precisely controlled to allow elimination from the body. Furthermore the elimination has to be demonstrated. Another risk is that these polymers may bio accumulate in other tissues or organs such as the liver spleen etc.

It is an object of the present invention to provide reduction sensitive biodegradable polymers that are enzymatically degradable to avoid the risk of premature degradation and consequently drug release even before the polymers gets to the target site.

Another object of the present invention is to provide reduction sensitive polyesteramides based on biodegradable and non-toxic building blocks to achieve triggered intracellular delivery of bioactive agents.

The object of the present invention is achieved by providing a biodegradable polyesteramide (PEA) comprising disulphide linkages in the backbone of the PEA, further referred to as PEA-SS.

More preferably the biodegradable polyesteramide comprises alpha-amino acids, diols, aliphatic dicarboxylic acids and optionally diamines whereby at least one of the building blocks of the dicarboxylic acids, diols, or diamines comprises disulphide linkages.

The term "disulphide linkages" refers to a disulfide bond which is a covalent bond. The linkage is also called an SS-bond or disulfide bridge, (R—S—S—R). The "disulphide linkages" are present in the backbone of the PEA.

The term "backbone" refers to the main chain of a polymer comprising series of covalently bounded atoms that together create the continuous chain of the polymer.

The term "biodegradable" refers to material which is capable of being completely or substantially degraded or eroded when exposed to an in vivo environment or a representative in vitro. A polymer is capable of being degraded or eroded when it can be gradually broken-down, resorbed, absorbed and/or eliminated by, for example, hydrolysis, enzymolysis, oxidation, metabolic processes, bulk or surface erosion, and the like within a subject.

The PEA-SS of the present invention surprisingly show a good stability in circulation and in extracellular fluids. Moreover PEA-SS starts to degrade fast once present in the cellular compartments such as the cytoplasm and the nucleus of the cells because they are enzymatically degradable. In this case premature drug release is prevented. This means that a lower concentration of drugs can be used which will minimize or avoid side effects. The degradation products of PEA-SS are moreover readily cleared or metabolised by the body since they comprise amino acids, and aliphatic or cycloaliphatic diols and diacids.

The polyesteramides of the present invention comprise ester groups, amide groups and disulphide linkages. At least a building block of the polyesteramide comprises a S—S linkage. The disulphide linkage can be introduced via the dicarboxylic acids, the diol- or the diamine building blocks. Specific examples of such building blocks are bis(2-hydroxyethyl disulphide), cystamine or dithiodipropionic acid as shown in below formula's.

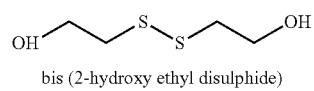

bis (2-hydroxy ethyl disulphide)

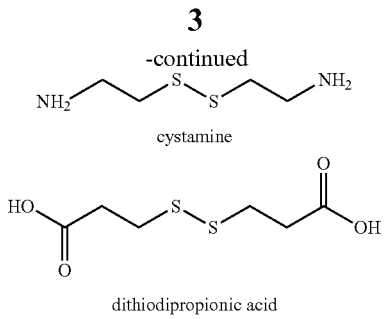

cystamine dithiodipropionic acid

Biodegradable polyesteramides are known in the art, in particular α-amino acid-diol-diester based polyesteramides (PEA) are known from G. Tsitlanadze, et al. J. Biomater. Sci. Polym. Edn. (2004) 15:1-24. These polyesteramides provide a variety of physical and mechanical properties as well as biodegradable profiles which can be adjusted by varying three components in the building blocks during their synthesis: naturally occurring amino acids and, therefore, hydrophobic alpha-amino acids, diols and aliphatic dicarboxylic acids.

In Biomacromolecules 2011, 12, 3243-3251, from A. Ghaffar, G. J. J. Draaisma, G. Mihov, A. A. Dias, P. J. Schoenmakers and Sj. van der Wal, PEA polymers were subjected to enzymatic degradation conditions. The PEA polymer were found to degrade at a steady rate with enzymes. A lack of significant changes in the average molecular weight of the remaining polymer strongly suggested that surface erosion occurred during the enzyme-mediated degradation. Furthermore, no accumulation of acidic byproducts was observed.

In the body, physiological fluids are not highly reductive, within cells that a more reductive environment is encountered. In an intracellular environment reduction occurs due to thiol-disulphide exchange reactions that occur in living cells. A biologically abundant thiol that may trigger the exchange reaction is glutathione tripeptide-g-glutamyl-cysteine-glycine (GSH) and glutathione disulphide (GSSG). GSH and GSSG are present in redox equilibrium in the mitochondria, nuclei and extracellular space.

In body fluids and in extracellular fluids low concentrations of GSH are present, typically these concentration vary from 2-20 uM. However intracellular the concentration of GSH varies typically from 0.5-10 mM due to NADPH and glutathione reductase that maintain reducing environment in cells. It is this difference in reductive potential, intercellular versus extracellular, that is used for intracellular drug delivery.

The reduction sensitive biodegradable polyesteramides according to the invention more preferably comprise at least one or a combination of the following structural formulas I, II or III.

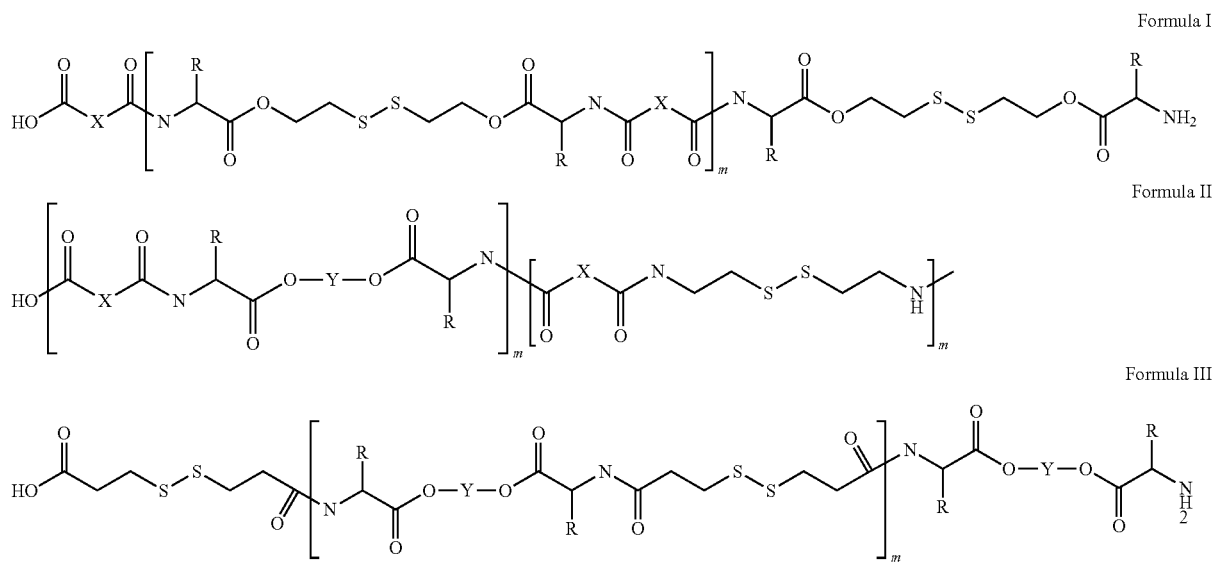

Wherein m varies from 5 to 300 and whereby

Y is independently selected from the group consisting of aliphatic or cycloaliphatic hydrocarbons, selected from the group consisting of ($C_2$-$C_{20}$) aliphatic or cycloaliphatic hydrocarbons.

X is independently selected from the group consisting of aliphatic, cycloaliphatic or aromatic hydrocarbons.

R is independently selected from the group consisting of a side chain residue of alpha-amino acids with positively charged groups, a side chain residue of amino acids with negatively charged groups, a side chain residue of amino acids with uncharged side groups or a side chain residue of amino acids with hydrophobic groups.

More preferably R is independently selected from the group consisting of a side chain residue of amino acids with positively charged groups chosen from arginine, histidine or lysine, a side chain residue of amino acids with negatively charged groups chosen from aspartic acid or glutamic acid, a side chain residue of amino acids with uncharged side groups chosen from serine, threonine, asparagine, glutamines, cysteine, seleno cysteine, glycine and proline or a side chain residue of aminoacids with hydrophobic groups chosen from alanine, valine, isoleucine, leucine, methionine, tyrosine, tryptophan or phenylalanine. Most preferably R is selected from the side chain residue of phenylalanine or arginine.

More preferably Y is selected from $(C_2-C_{20})$alkylene, $(C_2-C_{20})$alkenylene, bicyclic-fragments of 1,4:3,6-dianhydrohexitols of structural formula (IV) and combinations thereof.

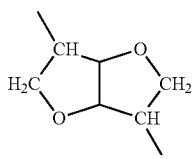

Formula (IV)

More preferably X is selected from $(C_2-C_{20})$ alkylene, $(C_2-C_{20})$ alkenylene. Most preferably X is selected from $-(CH_2)_4-$, $-(CH_2)_6-$ or $-(CH_2)_8-$.

In a preferred embodiment the biodegradable polyesteramide according to the present invention comprises structural formula I in which X is chosen from a $(C_2-C_{20})$ alkylene or $(C_2-C_{20})$ alkenylene and R is chosen from the side chain residue of arginine or phenylalanine. More preferably X is chosen from $-(CH_2)_4-$, $-(CH_2)_6-$ or $-(CH_2)_8-$, and R is chosen from the side chain residue of phenylalanine.

In another embodiment the biodegradable polyesteramide according to the present invention comprises structural formula II in which X is chosen from $(C_2-C_{20})$ alkylene or $(C_2-C_{20})$ alkenylene, Y is chosen from $(C_2-C_{20})$alkylene, $(C_2-C_{20})$ alkenylene, bicyclic-fragments of 1,4:3,6-dianhydrohexitols of structural Formula (IV) or combinations thereof and R is chosen from the side chain residue of arginine or phenylalanine.

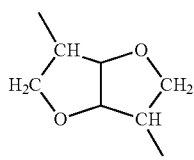

Formula IV

In still another embodiment the biodegradable polyesteramides according to the present invention comprises structural formula III in which Y is chosen from $(C_2-C_{20})$ alkylene, $(C_2-C_{20})$alkenylene, bicyclic-fragments of 1,4:3,6-dianhydrohexitols of structural Formula (IV) or combinations thereof and R is chosen from the side chain residue of arginine or phenylalanine.

The reduction sensitive biodegradable polyesteramides described herein can be fabricated in a variety of molecular weights and a variety of relative proportions of the building blocks in the backbone.

The in vitro and in vivo degradation of the biodegradable polyesteramides is well understood and the degradation products are naturally occurring compounds that are readily metabolized and/or eliminated by the patient's body. This is described in Journal of Chromatography A, 1286 (2013) 29-40, "A versatile system for studying the enzymatic degradation of multi-block polyesteramides", from A. Ghaffara, G. J. J. Draaismac, G. Mihovc, P. J. Schoenmakersa, Sj. van der Wal"

The polyesteramides of the present invention are especially useful for intracellular drug delivery. However in order to be effective, the biodegradable polyesteramides of the present invention preferably have to be of a size such that they are small enough to be taken up by the cells via endocytosis. The appropriate molecular weight for a particular use is readily determined by one skilled in the art. A suitable Mw will may vary from 500~20,000 g/mol, more preferably from 1,000~10,000 g/mol. Mw is measured via GPC in THF with polystyrene as standard.

The synthesis of the polyesteramides of the present invention (PEA-SS) may for example comprise the following three basic steps:

(i) Synthesis of disulfide containing di-p-toluenesulfonic acid salts of bis-L-phenylalanine ester (Phe(SS)-2TsOH);
(ii) Synthesis of di-p-nitrophenyl esters of adipic acid (Di-NP-adipate);
(iii) Solution polycondensation of monomers Phe(SS)-2TsOH and Di-NP-adipate at different molar.

The preparation of the reduction sensitive PEA's is further disclosed in the examples.

The present invention further relates to a drug delivery composition comprising the reduction sensitive polyesteramides of the present invention. The composition may further comprise a bioactive agent. Preferably the drug delivery composition comprises an anti-cancer agent. The drug delivery composition according to the present invention is especially useful for intracellular delivery of anti-cancer agents.

Examples of anticancer agents are adriamycin, aldesleukin, allopurinol, altretamine, amifostine, anastrozole, asparaginase, betamethasone, bexaroten, bicalutamide, bleomycin, busulfan, capecitabine, carboplatin, carmustine, chlorambucil, cisplatin, cladribine, conjugated estrogen, cortisone, cyclophosphamide, cytarabine, dacarbazine, daunorubicin, dactinomycin, denileukin, dexamethasone, discodermolide, docetaxel, doxorubicin, eloposidem, epirubicin, epoetin, epothilones, estramustine, esterified estrogen, ethynyl-estradiol, etoposide, exemestane, flavopirdol, fluconazole, fludarabine, fluorouracil, flutamide, floxuridine, gemcitabine, gemtuzumab, goserelin, hexamethylmelamine, hydrocortisone, hydroxyurea, idarubicin, ifosfamide, interferon, irinotecan, lemiposide, letrozole, leuprolide, levamisole, levothyroxine, lomustine, mechlorethamine, melphalan, mercaptopurine, megestrol, methotrexate, methylprednisolone, methyltestosterone, mithramycin, mitomycin, mitotane, mitoxantrone, mitozolomide, mutamycin, nilutamide, paclitaxel, pamidronate, pegaspargase, pentostatin, plicamycin, porfimer, prednisolone, procarbazine, rituximab, sargramostim, semustine, streptozocin, tamoxifen, temozolamide, teniposide, testolactone, thioguanine, thiotepa, tomudex, topotecan, toremifen, trastumuzab, tretinoin, semustine, streptozolocin, valrubicin, verteprofin, vinblastine, vincristine, vindesine, vinorelbine, and salts thereof, esters thereof, hydrates thereof, polymorphs thereof and isomers thereof.

The bioactive agent can however be any agent which is a therapeutic, prophylactic, or diagnostic agent. Such bioactive agent may include without any limitation small molecule drugs, peptides, proteins, DNA, cDNA, RNA, sugars, lipids and whole cells. The bioactive agents can have antiproliferative or anti-inflammatory properties or can have other properties such as antineoplastic, antiplatelet, anti-coagulant, anti-fibrin, antithrombotic, antimitotic, antibiotic, antiallergic, or antioxidant properties. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-0-(3-hydroxy)propyl-rapamycin, 40-O-[2-(2-hydroxy)ethoxy] ethyl-rapamycin, and 40-0-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia AND Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hb/nia platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck AND Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, dietary supplements such as various vitamins, and a combination thereof. Examples of anti-inflammatory agents including steroidal and nonsteroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck AND Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting.

The present invention further relates to a drug delivery system comprising the polyesteramide (PEA-SS) of the present invention or the drug delivery composition according to the present invention. The drug delivery system for example comprises rods, fibers, woven fabrics, micro- or nanoparticles, micelles, liposomes, polymerosomes, micro- and nanogels, polymerosomes or nanotubes.

A preferred drug delivery system comprises micro- or nanoparticles. The average diameter of the particles given by the Fraunhofer theory in volume percent ranges from 10 nm to 1000 µm. The preferred average diameter depends on the intended use. For instance, in case the particles are intended for use as an injectable drug delivery system, in particular as an intravascular drug delivery system, an average diameter of up to 20 m, in particular of 1 to 40 µm may be desired.

It is envisaged that particles with an average diameter of less than 1000 nm are nano-particles. Typically nanoparticles with a size of less than 800 nm, in particular less than 500 nm are useful for intracellular purposes. For such purposes, the average diameter preferably is at least 20 nm or at least 30 nm.

In other applications, larger dimensions may be desirable, for instance a diameter in the range of 1-100 µm or 10-100 µm.

The size of the nanoparticles was determined by a Zetasizer Nano-ZS from vern Instruments equipped with a 633 nm He—Ne laser using backscattering detection at C.

If particles are too small or non-analyzable by light scattering which may be the case with nanoparticles because of their optical properties, then scanning electron microscopy (SEM) or transmission electron microscopy (TEM) can be used.

The polyesteramides, the drug delivery composition and the drug delivery systems of the present invention can be used in the medical field especially in drug delivery in the field of management of pain, MSK, ophthalmology, cancer treatment, vaccine delivery compositions, dermatology, cardio-vascular field, orthopedics, spinal, intestinal, pulmonary, nasal, or auricular.

FIGURES

FIG. 1: $^1$H NMR spectrum of PEA-SS1 (400 MHz, DMSO-$d_6$).

Figure 2:
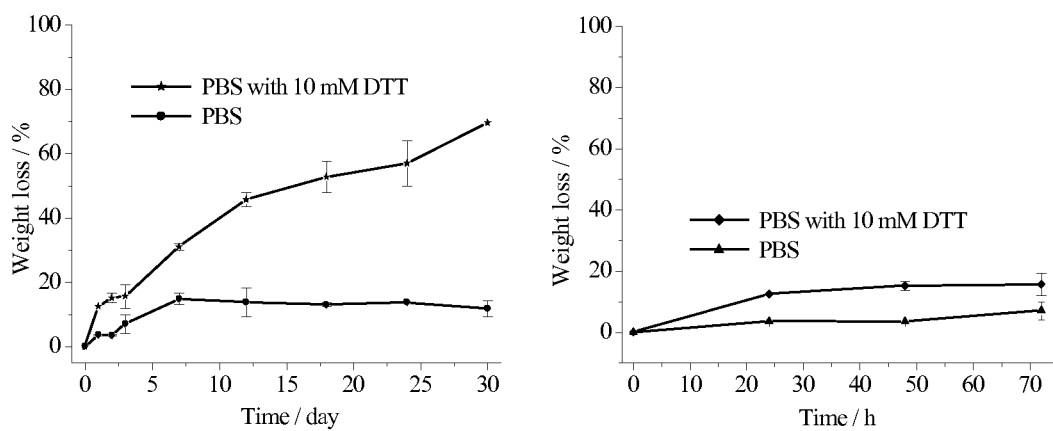

FIG. 2: Percentage of PEA (SS) film weight loss as a function of degradation time (days) in α-Chymotrypsin (0.1 mg/mL) and DTT (10 mM) in PBS at 37° C. and 120 rpm. PBS buffer serves as the control. (A) weight loss in 30 d; (B) weight loss in the first 3 d.

Figure 3:
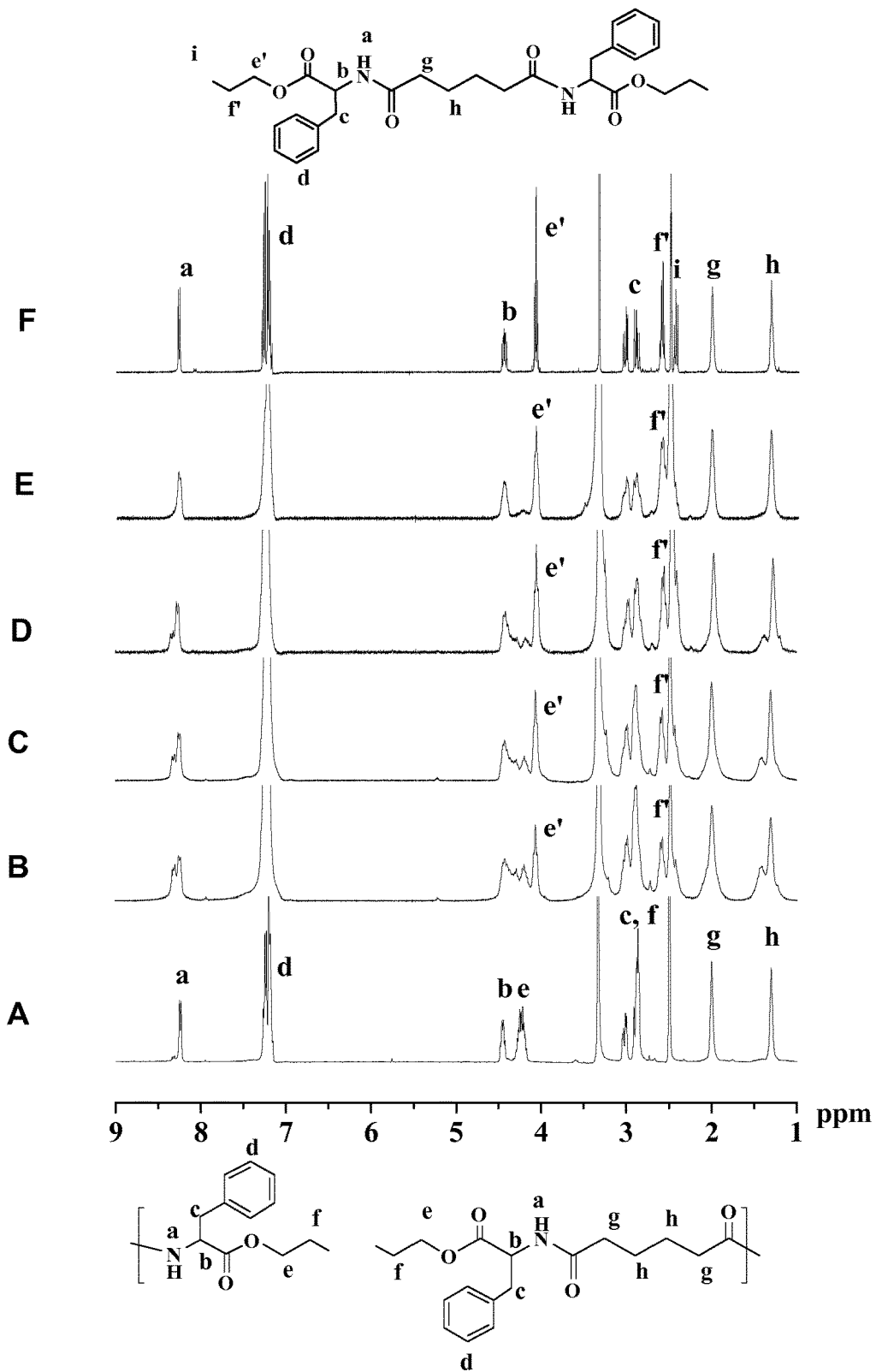

FIG. 3: $^1$H NMR spectra of PEA(SS) before (A) and after treatment with DTT for 2.5 h (B), 5 h (C), 8 h (D), 11 h (E) and 23 h (F) (DMSO-$d_6$, 400 MHz).

Figure 4:
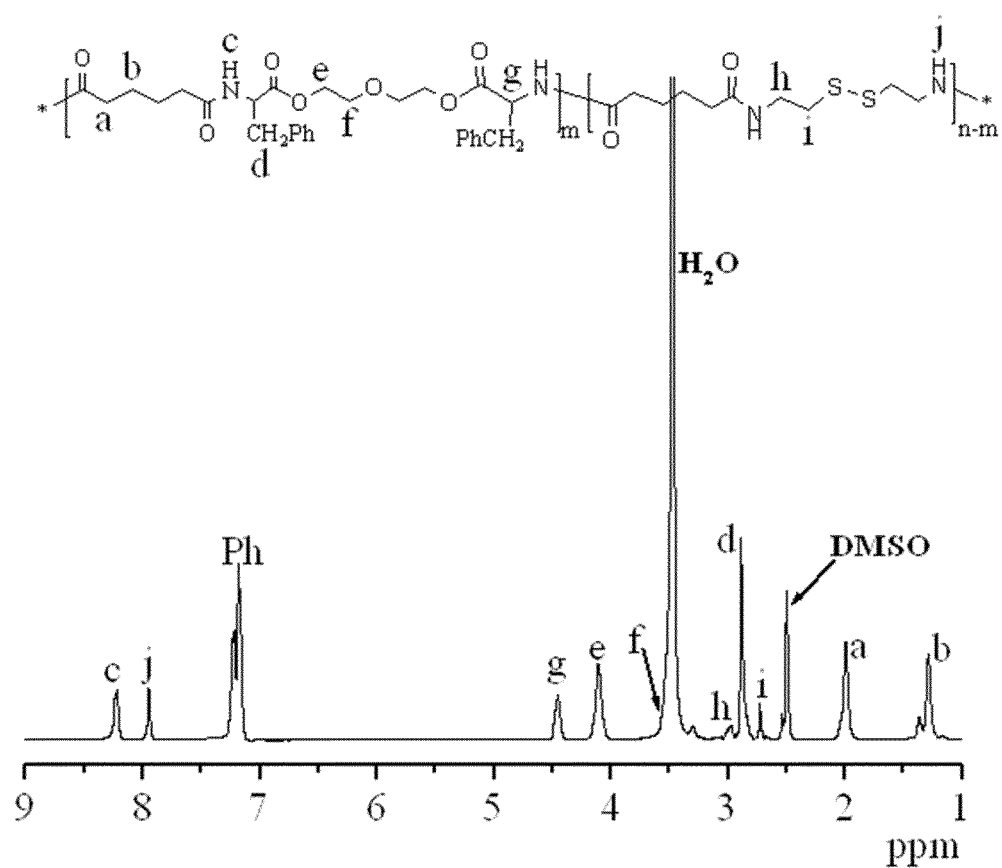

FIG. 4: $^1$H NMR of PEA-SS(P2EG/Cys=88/12) in DMSO-$d_6$ (400 MHz).

Figure 5:
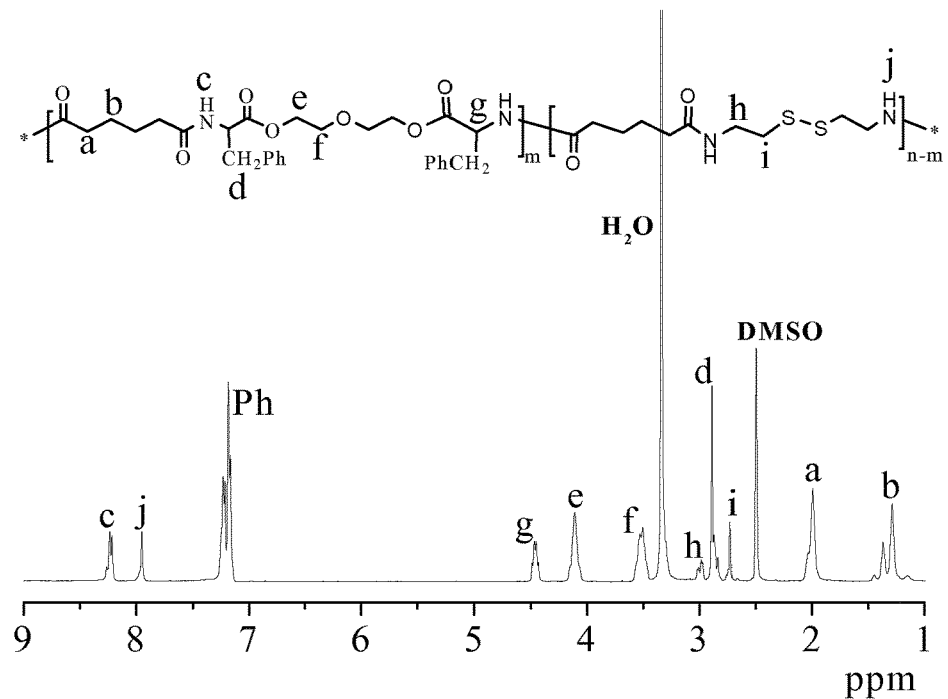

FIG. 5: $^1$H NMR of PEA-SS(P2EG/Cys=78/22) in DMSO-$d_6$ (400 MHz).

Figure 6:
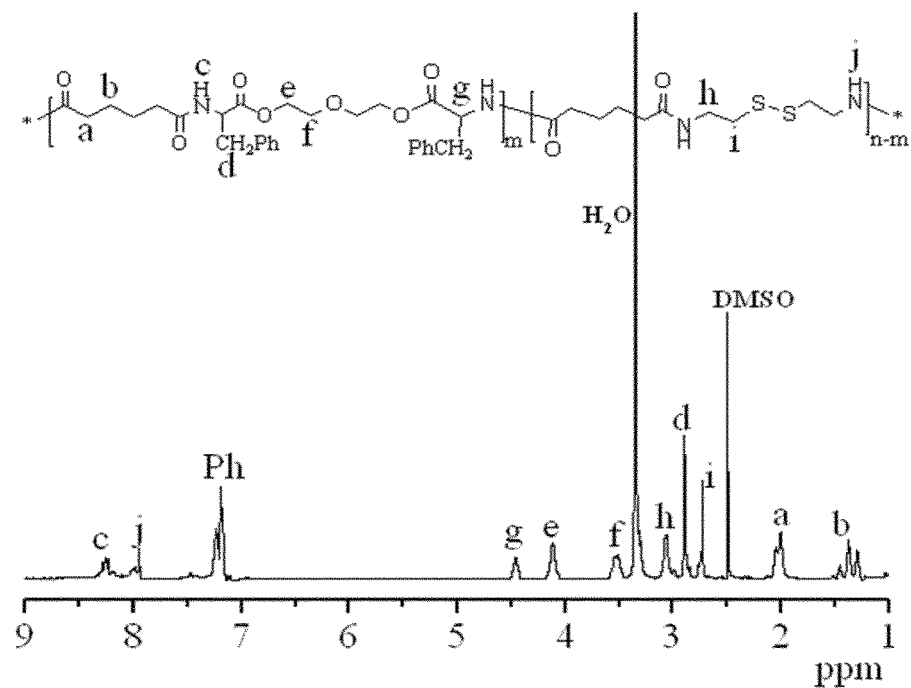

FIG. 6: $^1$H NMR of PEA-SS(P2EG/Cys=57/43) in DMSO-$d_6$ (400 MHz).

Figure 7:
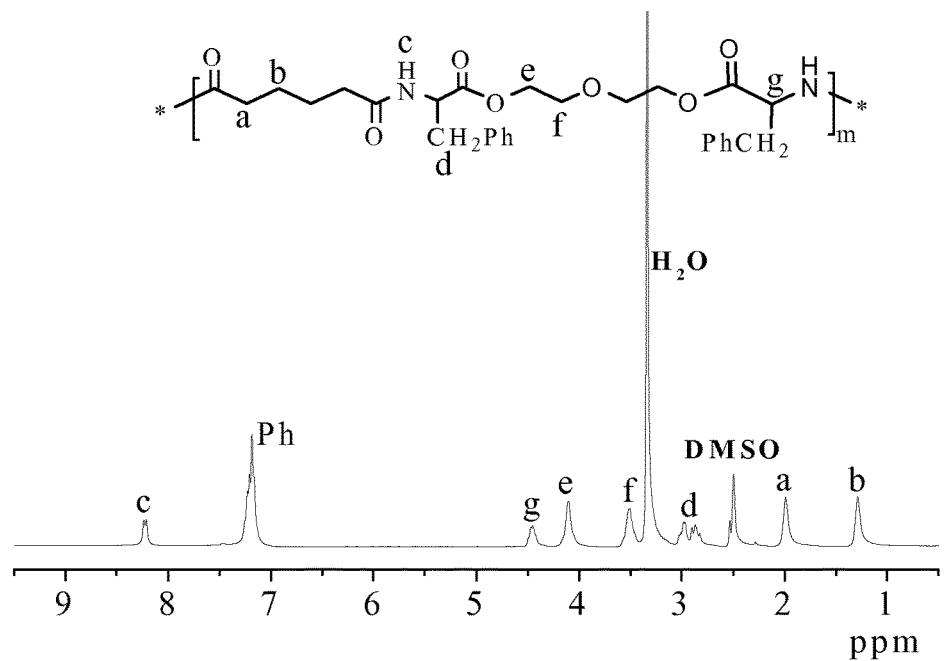

FIG. 7: $^1$H NMR of PEA in DMSO-$d_6$ (400 MHz).

Figure 8:
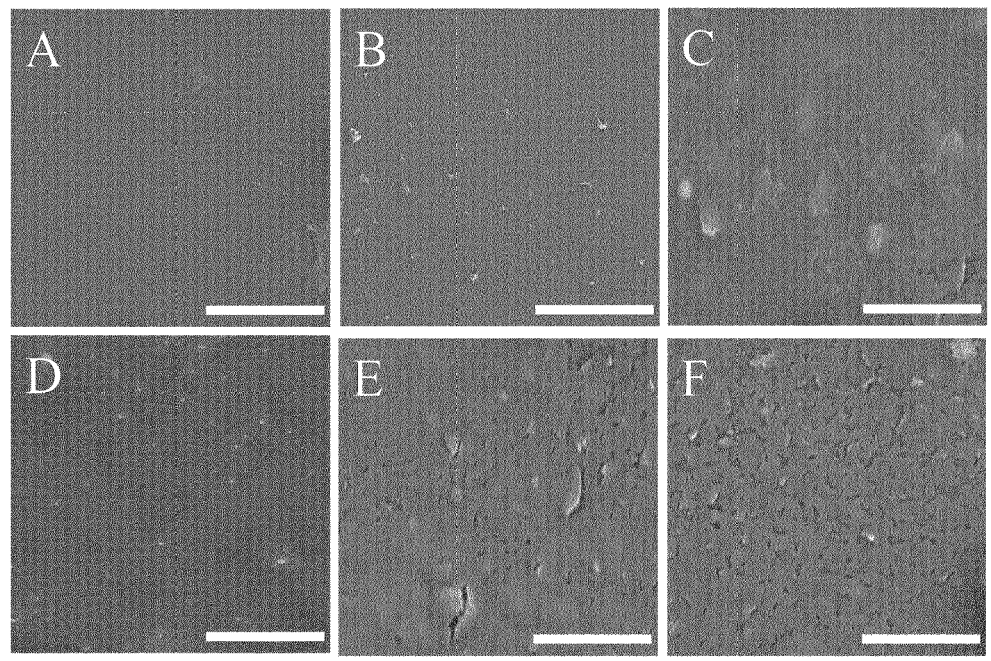

FIG. 8: SEM images of PEA and PEA-SS(P2EG/Cys=78/22) films at. The bars represent 20 um. (A) Original film of non-reduction-sensitive PEA polymers; (B) incubation in PBS for 1 day; (C) incubation in PBS for 4 day. (D) Original film of reduction-sensitive PEA-SS polymers; (E) incubation in 10 mM DTT for 12 h; (F) incubation 10 mM DTT for 24 h.

Figure 9:
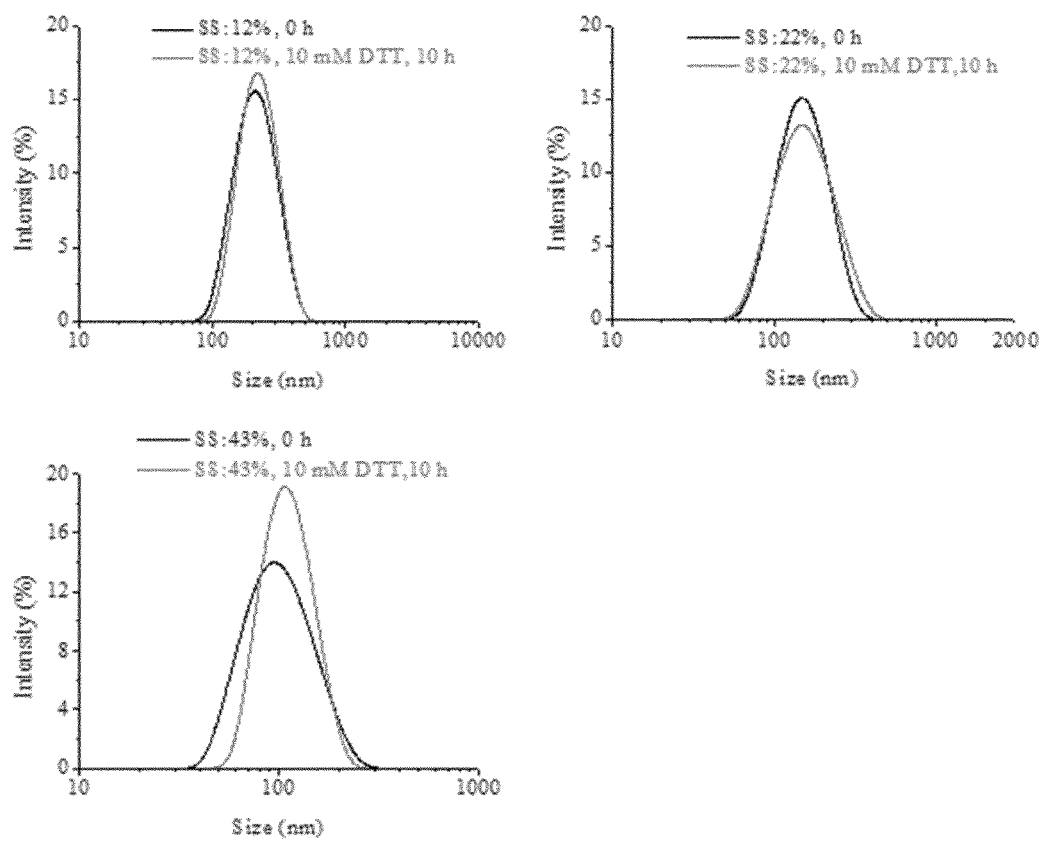

FIG. 9: The size change of different ratios of nanoparticles upon the addition of 10 mM DTT in PBS (pH 7.4, 10 mM, NaCl 100 mM).

Figure 10:
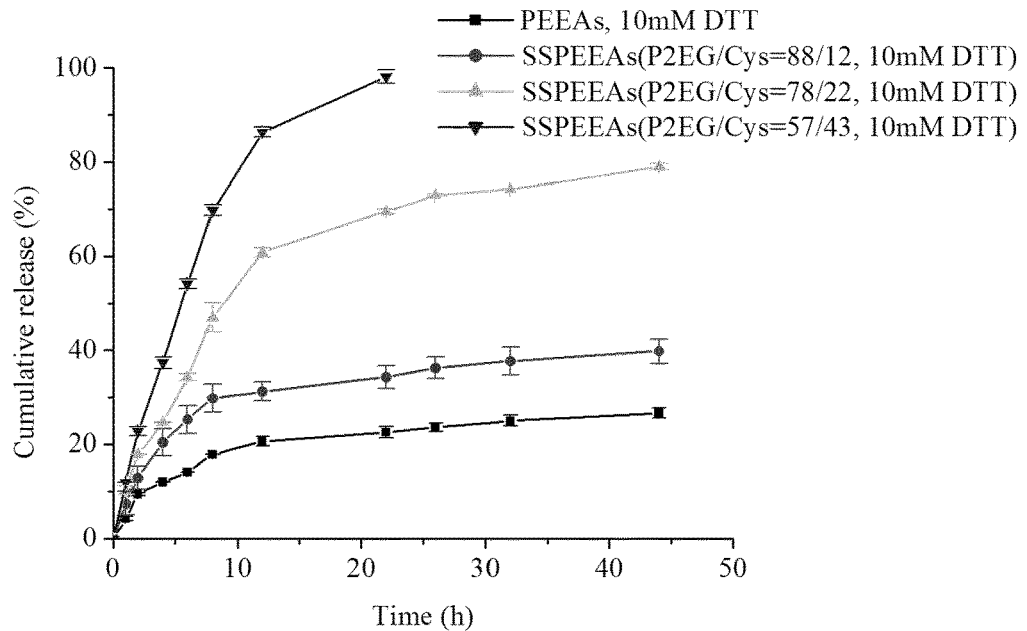

FIG. 10: FITC-BSA release from nanoparticles in the presence of 10 mM DTT.

Figure 11:
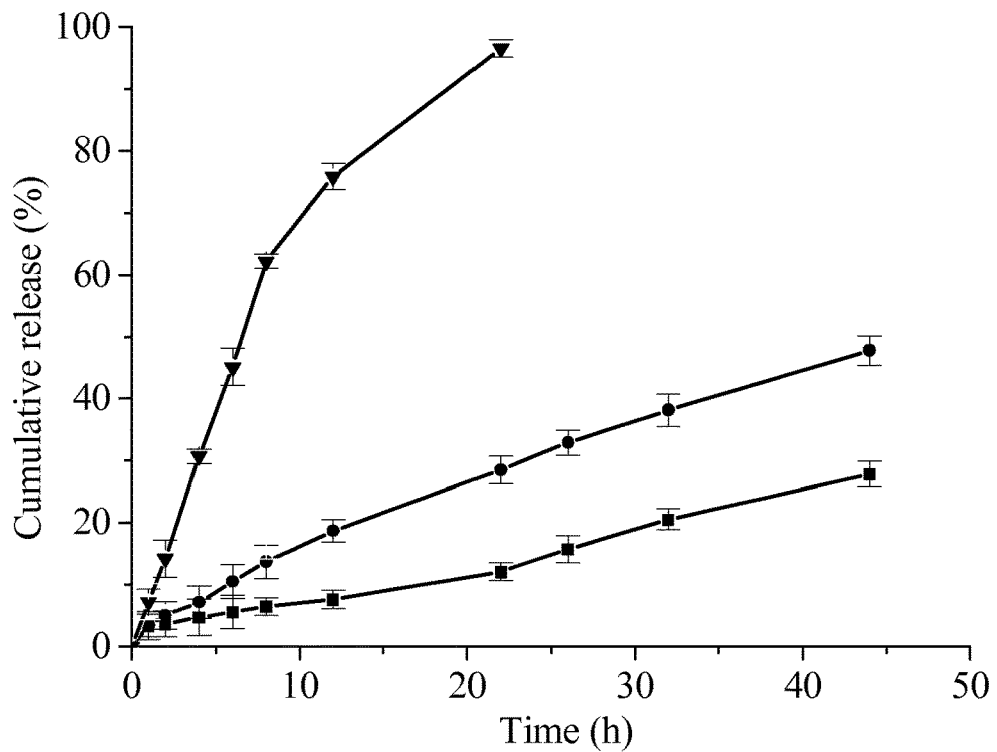

FIG. 11: FITC-CC release from nanoparticles in the presence of 10 mM DTT.

Figure 12:
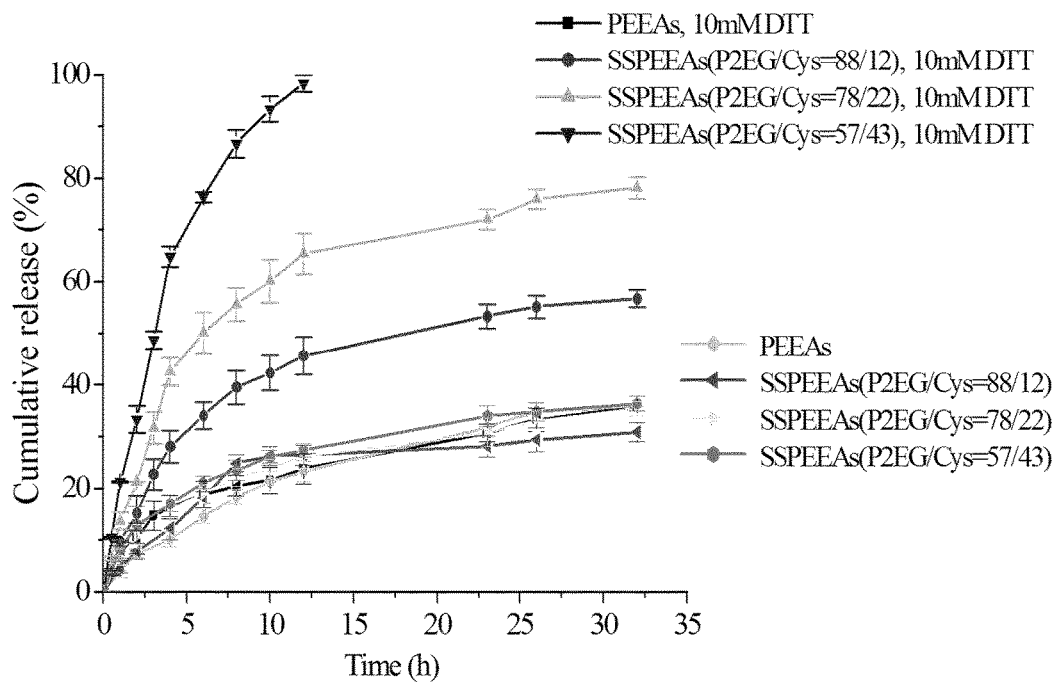

FIG. 12: DOX release from nanoparticles.

Figure 13:
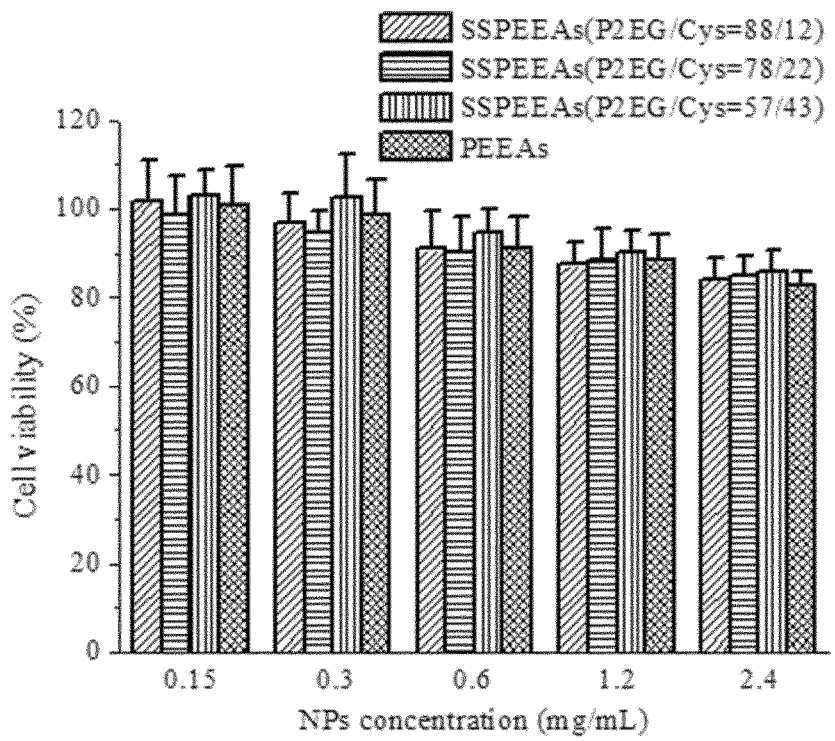

FIG. 13: MTT assays of empty nanoparticles.

Figure 14A:
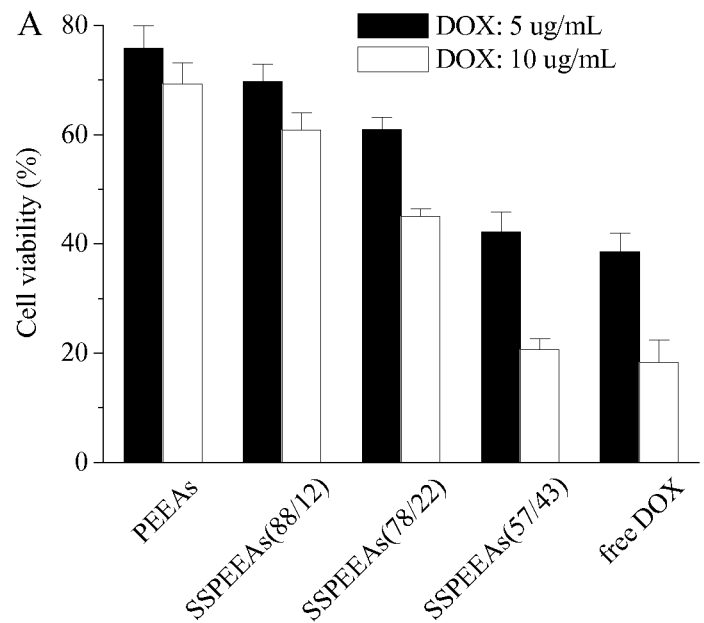

FIG. 14A+B: MTT assays of reduction-sensitive DOX-loaded PEA nanoparticles, (A) Hela cells; (B) MCF-7 cells. The incubation time was 48 h.

Figure 15:
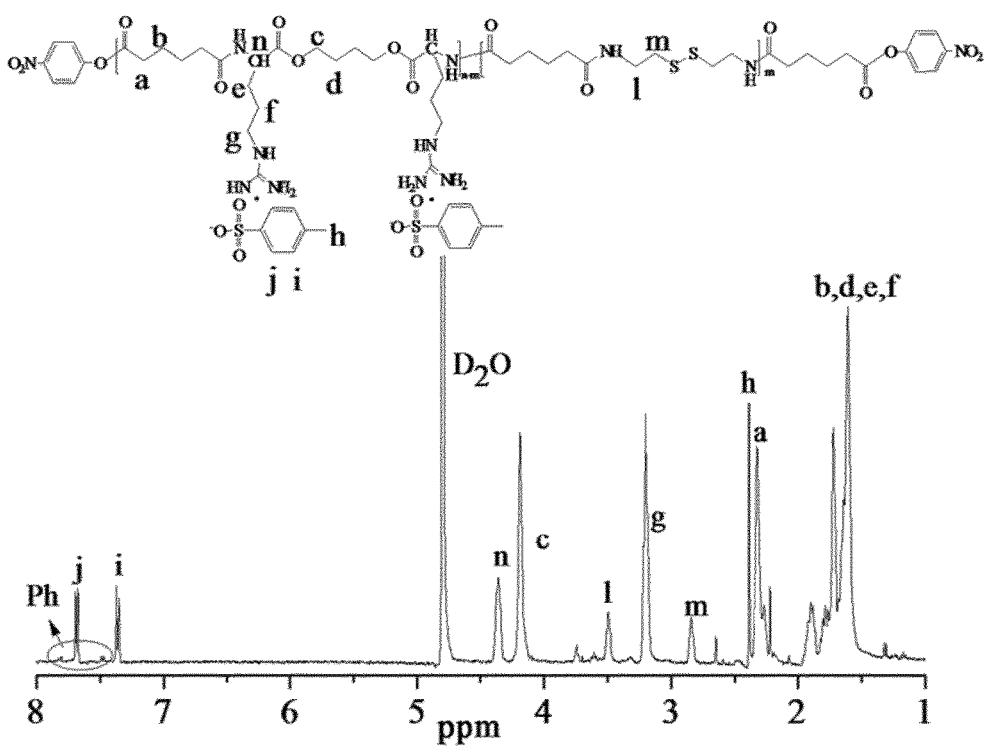

FIG. 15. 1H NMR of L-Arg-4 based reduction-sensitive poly (ester amide)s in D2O (400 MHz)

EXAMPLES

Example 1: Synthesis of Reduction-Sensitive Di-p-Toluenesulfonic Acid Salts of Bis-L-Phenylalanine Ester Scheme 1: Synthesis of reduction-sensitive di-p-toluenesulfonic acid salts of bis-L-phenylalanine ester (Phe(SS)-2TsOH).

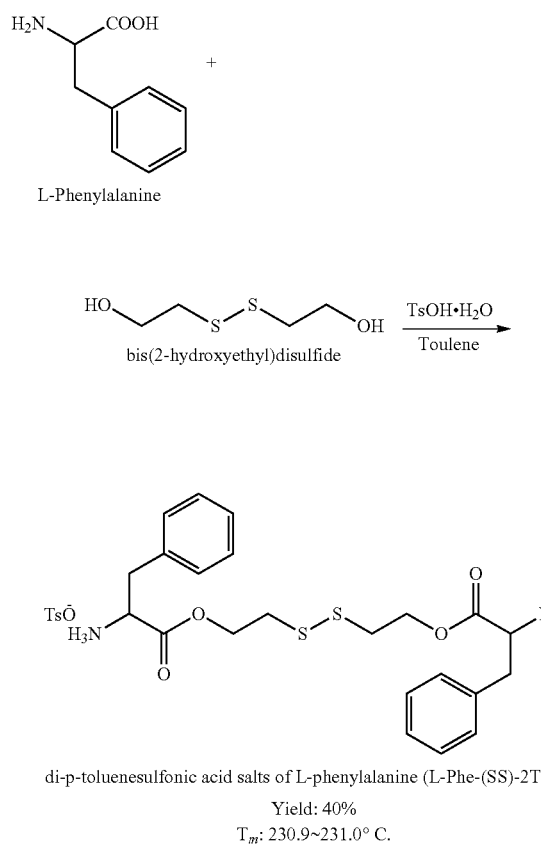

di-p-toluenesulfonic acid salts of L-phenylalanine (L-Phe-(SS)-2TsOH)
Yield: 40%
$T_m$: 230.9~231.0° C.

L-Phenylalanine (L-Phe, 6.000 g, 0.0363 mol), bis(2-hydroxyethyl)disulfide (HES, 2.546 g, 0.0165 mol) and p-toluenesulfonic acid monohydrate (6.909 g, 0.0363 mol) in 92 mL of toluene (20 mL for Dean-Stark) were placed in a flask equipped with a magnetic stirrer, a Dean-Stark apparatus and a CaCl2 drying tube. The solid-liquid reaction mixture was heated to reflux for 24 h until 0.95 mL of water was evolved and the reaction mixture changed to ivory-white. 7 mL ethanol (1/10 v. of toluene) was added after the reaction mixture was cooled to 60° C. below and then cooled to r.t., filtered, washed twice using mixture of toluene and ethanol (10/1 v.) and dried in vacuum at r.t. The product Phe(SS)-2TsOH was purified by recrystallization from methanol/water (1:1) three times. Yield: 40%. 1H NMR (400 MHz, DMSO-d6): δ 2.29 (6H, CH3-Ph-SO3-), 2.86 (4H, —CH2-S—S—), 3.11 (4H, Ph-CH2-), 4.33 (6H, 4H of —COO—CH2-CH2-S—S— and 2H of +H3N—CH(CH2PH)—COO—), 7.10-7.49 (18H, Ph), 8.41 (6H, +H3N—CH(CH2PH)—). FTIR (cm-1): 3000 (—NH3+), 1735[—C(O)—], 1450, 1500 and 1600 (Ph), 1202 (—SO3-). DSC: Tm=231° C.

Example 2: Synthesis of Di-p-Nitrophenyl Ester of Adipic Acid

Scheme 2: Synthesis of di-p-nitrophenyl ester of adipic acid. (Di-NP-Adipate)

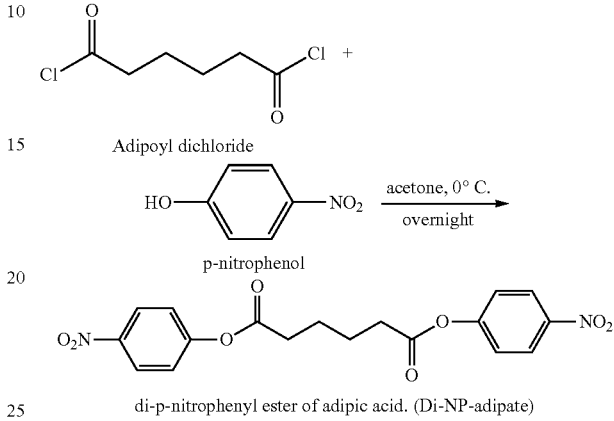

di-p-nitrophenyl ester of adipic acid. (Di-NP-adipate)

The monomer Di-NP-Adipate was obtained via reacting adipoyl dichloride with p-nitrophenol (FIG. 3). Briefly, to a solution of p-nitrophenol (16.777 g, 0.1206 mol) and triethylamine (16.810 mL, 0.1206 mol) in 200 mL of acetone, a solution of adipoyl dichloride (10.982 g, 8.715 mL, 0.0600 mol) in 80 mL acetone was added dropwise at 0° C. After completion of addition, the reaction mixture was continued stirring for 2 h, then warmed to r.t. and proceeded overnight. Finally, the resulting monomer was obtained by pouring the reaction mixture into 1.6 L of ultra-pure water, filtration, washing twice with water, drying in vacuum at 50° C. overnight and recrystallization from ethyl acetate three times. Yield: 71%. 1H NMR (400 MHz, DMSO-d6): δ 2.73 (4H, —OCO—CH2-), 1.76 (4H, —OCO—CH2-CH2-), 7.46 and 8.29 (4H, —O-Ph-NO2). DSC: Tm=124.1-124.5° C.

Example 3: Synthesis of Reduction-Sensitive L-Phenylalanine Based Polyesteramides (PEA-SS1)

PEA-SS1 having repeat disulfide bonds was synthesized via solution polycondensation of Phe(SS)-2TsOH and dinitrophenyl ester of adipic acid (Di-NP-adipate). The synthetic pathway is shown in reaction scheme 3. Take balanced PEA (SS) (1:1) synthesis as an example. Briefly, to a Schlenk bottle equipped with a magnetic stir bar was charged Phe (SS)-2TsOH (0.7098 g, 0.895 mmol), Di-NP-adipate (0.3473 g, 0.895 mmol), Et3N (0.275 mL, 1.969 mmol) and 0.471 mL of DMF. After 20 min degasing with nitrogen flow, the reaction vessel was sealed and immersed in an oil bath thermostated at 70° C. The polymerization was allowed to proceed for 48 h. The resulting polymer was isolated by dilution with DMF, precipitation in ethylacetate two times to remove nitrophenol, precipitation in water to remove Et3N-TsOH and freeze-drying for 2 days.

In order to verify the actual chemical structure of the new PEA(SS), its 1H NMR and FTIR spectra was obtained (FIG. 1). As shown in FIG. 1, peaks assignable to both Di-NP-adipate (b 2.00 and 1.33) and Phe(SS) (2.86, 3.01, 4.24, 4.45, 7.20 and 8.24) were present in the 1H NMR spectrum.

Importantly, comparing the integrals of signals at δ 2.00 and 4.45 pointed to a 1:1 equivalent polycondensation of Di-NP-adipate and Phe(SS)-2TsOH. FTIR spectrum showed the characteristic absorption bands of amide groups (~1638 cm-1), NH stretch of amide groups (3430 cm-1) and C=O stretch of ester groups (~1735 cm-1).

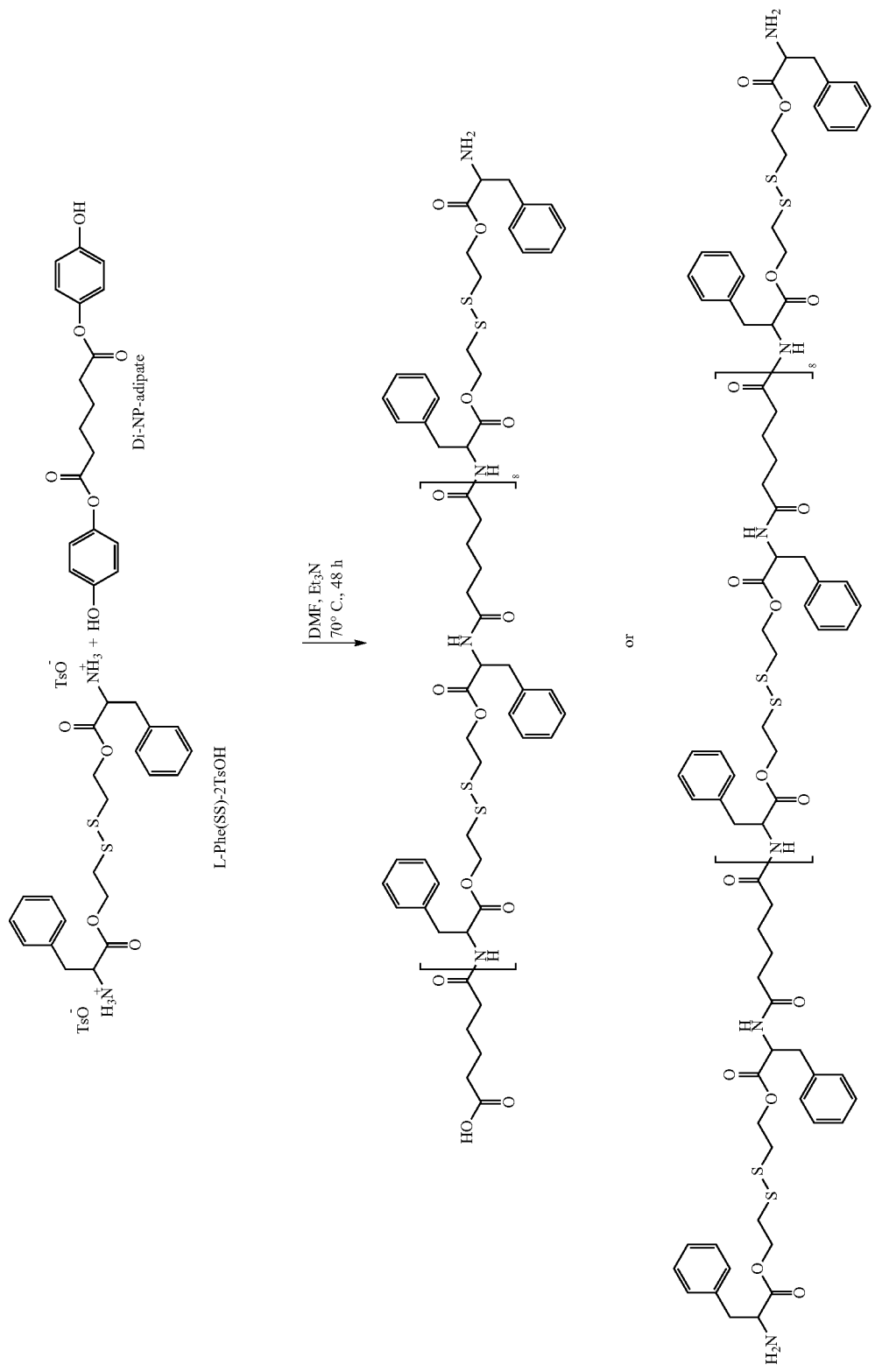
Scheme 3: Synthesis of reduction-sensitive L-Phenylalanine based poly(ester amide)s.

GPC curve showed a decreasing trend of PDI (Poly Dispersity Index) with the decrease of equivalent ratio as represented in below Table 1.

TABLE 1

| Equivalent | $M_{n,UV}{}^a$/ kDa | $M_{n,GPC}$/ kDa | $M_{w,GPC}$/ kDa | PDI | $T_g$/° C. | Yield/% |
|---|---|---|---|---|---|---|
| 1.0 eqv | — | 12.1 | 33.0 | 2.73 | — | 70.9 |
| 1.0 eqv | 58.3 | 22.8 | 47.7 | 2.10 | 39.49 | 82.5 |
| 0.98 eqv | 24.5 | 22.3 | 44.1 | 1.97 | 35.22 | 65.7 |
| 0.96 eqv | 13.1 | 21.8 | 36.6 | 1.68 | 37.03 | 63.0 |
| 0.93 eqv | 9.3 | 16.6 | 24.0 | 1.45 | 37.54 | 62.9 |

Example 4: In Vitro Enzymatic and Reductive Biodegradation of Disulfide Containing Poly(Ester Amide)s To study the biodegradability of PEA(SS) polymers, PEA(SS) films were drop-cast from a 40 mg/mL chloroform solution onto glass microscope slides (1 cm×1 cm), and the solvent was allowed to evaporate overnight at r.t. Then the coated slides were placed into the 24-well cell plate and further dried in vacuo at r.t. for 2 d.

The coated dried slides (each in duplicate) were immersed in 1 mL of PBS buffer (pH 7.4 0.2 g KCl, 0.2 g $KH_2PO_4$, 1.15 g $Na_2HPO_4$, 8.0 g NaCl in 1 L, containing 0.05% (w/v) sodium azide to inhibit bacterial growth), or PBS buffer with α-chymotrypsin (0.1 mg/mL), or PBS buffer with 10 mM DTT in 24-well cell plate and incubated at 37° C. and 120 rpm. The degradation medium was refreshed every 24 h. At predetermined intervals, the remaining polymer samples (on slides) were collected via aspiration of the incubation medium and following rinsing of the wells three times for 5 min with distilled water. The collected samples were then dried in vacuo at r.t. to a constant weight. The degree of the degradation was estimated from the weight loss of the PEA(SS) film based on the following formula:

$$\text{Weight loss }(\%) = \left[1 - \frac{\text{(weight of the film+ slide)} - \text{(weight of the slide)}}{\text{(initial weight of the film+ slide)} - \text{(weight of the slide)}}\right] \times 100\%$$

The degradation kinetics of PEA(SS) films in PBS buffer (pH 7.4), α-chymotrypsin solution (0.1 mg/mL) or DTT solution (10 mM) were illustrated FIG. 2.

In addition, the molecular weight of the PEA(SS) films after degradation was monitored via GPC.

TABLE 2

Weight loss and molecular weight of PEA(SS) films before and after incubation in different media.

| Polymer | Degradation Condition | Weight loss/% | $M_n$(GPC)/ kDa | $M_w$(GPC)/ kDa | PDI |
|---|---|---|---|---|---|
| PEA(SS) | Original polymer | 0 | 23.6 | 56.6 | 2.4 |
| | PBS-12 d | 14 | 20.0 | 48.7 | 2.4 |
| | 0.1 mg/mL α-Chymotrypsin-1 d | 70 | 22.4 | 53.9 | 2.4 |
| | 10 mM DTT-1 d | 12.5 | No signal | | |

$^1$H NMR and GPC measurements confirmed successful cleavage of disulfide bonds of each repeating unit to yield small molecules after 23 h. The resonances at δ 4.24 and 2.86 attributable to the methylene protons neighboring to the ester (—COO—CH$_2$—CH$_2$—SS—) and to the disulfide bond (—CH$_2$—SS—CH$_2$—) shifted to δ 4.08 and 2.60 respectively, which due to the disulfide bond is cleaved to thiol end groups. In addition, a new peak at δ 2.44 characteristic of thiol protons was detected as shown in FIG. 3.

The disulfide cleavage ratios of PEA(SS) polymer after 2.5, 5, 8, 11 and 23 h are calculated to be 46%, 55%, 70.5%, 86.5 and 100% via compare the integral ratio of peak e or f to peak b, respectively. Moreover, GPC revealed no signal for the polymer after 23 h treatment with DTT, which may be because the PEA(SS) polymer has been disrupted into small molecules completely (Table 3). FTIR measurement showed the same spectrum with initial PEA(SS) (FIG. 3), which indicated only disulfide bond cleaved during the reduction process.

TABLE 3

GPC results of PEA(SS) before and after DTT treatment.

| Sample | Mn (kDa) | Mw (kDa) | PDI |
|---|---|---|---|
| PEA(SS) | 22.8 | 47.7 | 2.1 |
| PEA(SS) + DTT | No signal | | |

Example 5: Synthesis of Di-p-Toluenesulfonic Acid Salts of Bis-L-Phenylalanine Esters (II)

Scheme 4: Di-p-toluenesulfonic acid salts of bis-L-phenylalanine esters were prepared according to the above.

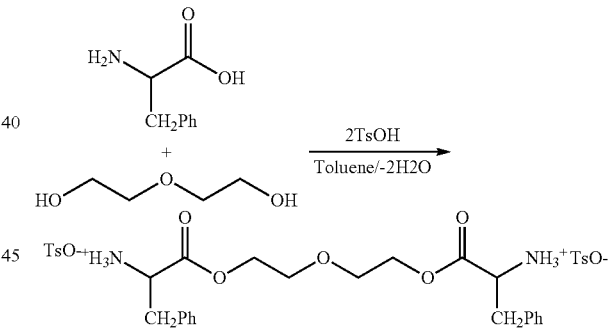

Typically, L-Phe (0.176 mol), p-toluenesulfonic acid monohydrate (0.176 mol), and diethylene glycol (0.08 mol) in 300 mL of toluene were placed in a flask equipped with a Dean-Stark apparatus, a $CaCl_2$ drying tube, and a magnetic stirrer. The solid-liquid reaction mixture was heated (ca. 140° C.) to reflux for 16 h. The reaction mixture was then cooled to room temperature. After the solvent was removed by rotary evaporation, the mixture was dried in vacuo overnight and finally purified by recrystallization from water 3 times. Thermal properties of synthesized monomer were characterized by a DSC 2920 (TA Instruments, New Castle, Del.). The measurement was carried out from 0 to 300° C. at a scanning rate of 10° C./min and nitrogen gas flow rate of 25 mL/min. TA Universal Analysis software was used for thermal data analysis. The melting point was determined at the onset of the melting endotherm. The melting point is 245° C.

The structure of the di-p-toluenesulfonic acid salt monomer was confirmed by FTIR and NMR spectra. The $^1$H NMR data of the monomer also showed characteristic signals of —CH$_2$—O—CH$_2$— ($^1$H: δ~3.50 ppm). The monomer was obtained as white powder, and the yield was about 63%.

FTIR (cm$^{-1}$): 1736 [—C(O)—], 1177 (—O—), 1127 (—CH$_2$—O—CH$_2$—). $^1$H NMR (DMSO-d$_6$, ppm, δ): 2.29 (6H, H$_3$C-Ph-SO$_3$—), 3.05, 3.10 (4H, PhCH$_2$—), 3.50 [4H, —(O)C—O—CH$_2$—CH$_2$—], 4.19 [2H, $^+$H$_3$NCH(CH$_2$Ph)-], 4.31 [4H, —(O)C—O—CH$_2$CH$_2$—], 7.11 to –7.49 [18H, Ph], 8.39 [6H, $^+$H$_3$N—CH(CH$_2$Ph)-].

Example 6: Solution Polycondensation of Toluene Sulfonate Di Ester of Phenylalanine, Di-Nitrophenyl Ester and Cystamine Dihydrochloride PEAs were prepared by solution polycondensation of di-p-toluenesulfonic acid diester salt with di-p-nitrophenyl ester and cystamine dihydrochloride, which involved four different ratios of phenylalanine and cystamine dihydrochloride (SS: 0%, 10%, 20% and 40%, SS represents cystamine dihydrochloride). The combinations attempted in this work shown in below scheme 5 explaining the synthesis of L-Phenylalanine Based PEAs.
A: containing cystamine dihydrochloride (PEA-SS);
B: containing no cystamine dihydrochloride (PEAs).

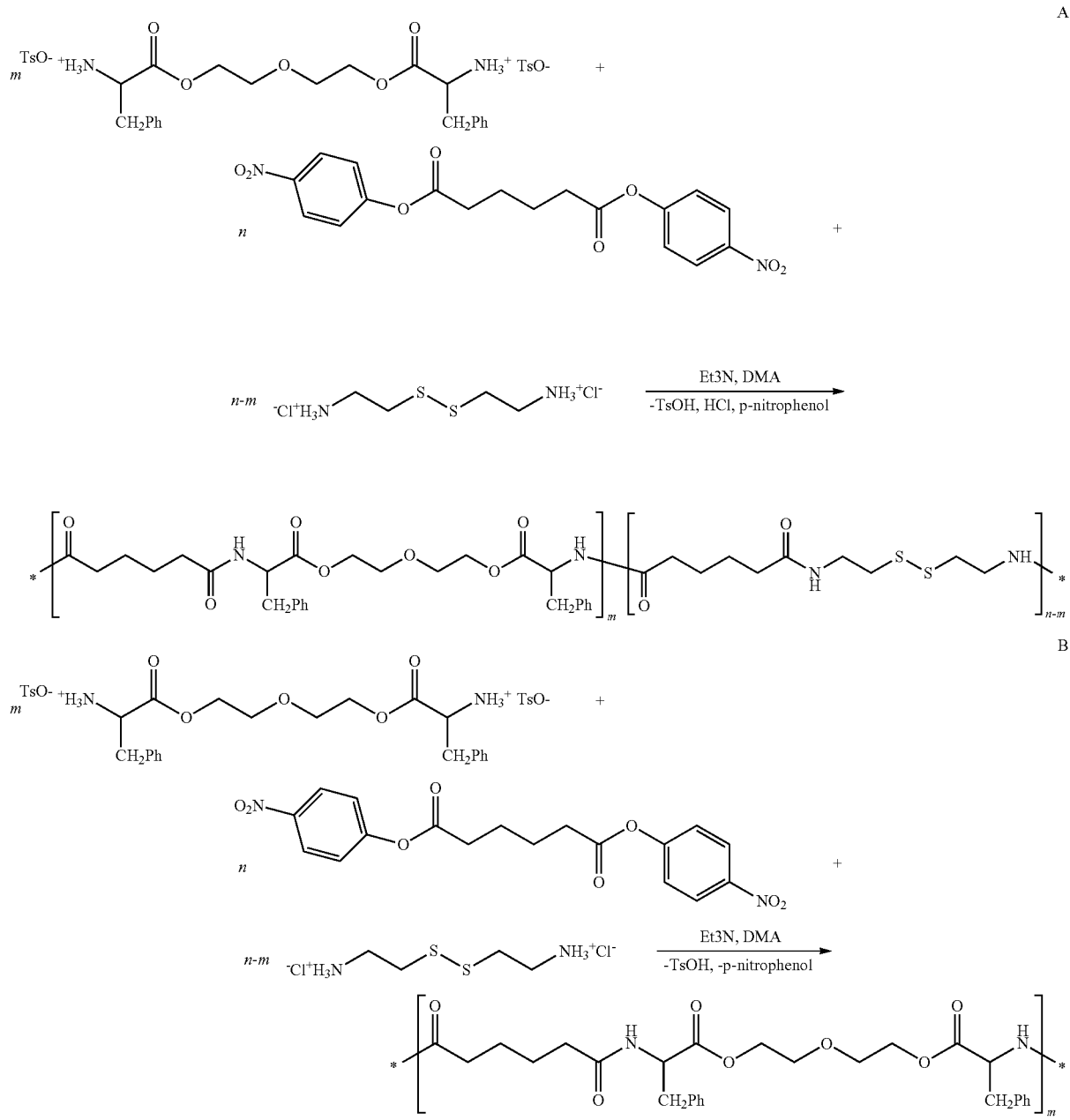

Table 4 summarizes the fundamental properties of the PEA-SS synthesized. All four PEA-SS were obtained in fairly good yields (61-72%). The number and weight averaged molecular weights ($M_n$ and $M_w$) of synthesized PEA-SS were determined by GPC, and DMF was used as eluent.

TABLE 4

Fundamental Properties of PEA-SS

| Polymer | Theoretical (molar ratio) m:n-m[b] | Experimental (molar ratio)[a] | $M_n$[c] | PDI | Yield (%) |
|---|---|---|---|---|---|
| PEA-SS (P2EG/Cys = 88/12) | 90:10 | 88/12 | 48000 | 1.4 | 64 |
| PEA-SS (P2EG/Cys = 78/22) | 80:20 | 78/22 | 38500 | 1.5 | 66 |
| PEA-SS (P2EG/Cys = 57/43) | 60:40 | 57/43 | 21900 | 1.7 | 72 |
| PEA | — | — | 25000 | 1.3 | 61 |

[a] determined by $^1$H NMR.
[b] m:n-m is the molar ratio of di-p-toluenesulfonic acid salts of L-phenylalanine ester to cystamine.
[c] Determined by GPC (DMF as the eluent, 1.0 mL/min, 30° C., polystyrene standards).

The $^1$H NMR spectra of four typical PEA-SS based on di-ethylene glycol are shown in FIGS. 4, 5, 6 and 7. The spectral data were fully in agreement with the anticipated chemical structure of the PEA polymers shown in Scheme 5.

Example 7: In Vitro Biodegradation of PEA-SS/PEA Copolymers

Biodegradation of PEA-SS/PEA copolymers were carried out in a small vial containing a small piece of dry PEA-SS/PEA film, (ca. 80 mg) and 10 mL of PBS buffer solution (pH 7.4, 10 mM,) consisting of 10 mM DTT or not. The vial was then incubated at 37° C. with a constant reciprocal shaking (100 rpm). At predetermined immersion durations, the film samples were removed from the incubation medium, washed gently with distilled water, and surface water was blotted by film paper and dry at room temperature. Scanning electron microscope (SEM) was employed to analyze the effect of biodegradation process on the surface morphology of PEA-SS/PEA polymers. The surface morphology changes of these PEA-SS/PEA film samples upon biodegradation are shown in FIG. 8. After 1 day and 4 days incubation in PBS buffer (pH 7.4, NaCl 100 mM), the PEA film samples showed little surface erosion. However, the PEA-SS film samples showed a significant biodegradation after 12 h and 24 h incubation in 10 mM DTT PBS buffer as evident by the appearance of rough or crater shaped eroded surface with more microscopic pores.

Example 8: Preparation of Nanoparticles

Nanoparticles were prepared by dialysis synthetic method with suitable size and narrow PDI (Table 5).

TABLE 5

Size and PDI results of nanoparticles.

| Nanoparticles | Size (nm) | PDI |
|---|---|---|
| PEA-SS(P2EG/Cys = 88/12) | 143 | 0.15 |
| PEA-SS(P2EG/Cys = 78/22) | 138 | 0.11 |
| PEA-SS(P2EG/Cys = 57/43) | 151 | 0.12 |
| PEA | 97 | 0.17 |

[a] SS represents Cystamine Dihydrochloride monomer.

The disulfide bonds containing PEA nanoparticles are reported to have reduction sensitivity in an intracellular mimicking environment. Here we investigated the responsiveness of the nanoparticles containing different ratios of disulfide bonds. We firstly followed the size change of the nanoparticles at different ratio in response to 10 mM DTT in PBS buffer (pH 7.4, 10 mM, NaCl 100 mM) by using DLS measurement. For the nanoparticles containing 10-40% SS, DTT (10 mM) treatment did not affect the size of the nanoparticles (FIG. 9).

Example 9: Preparation of Nanoparticles of PEA with and without Protein (FITC-BSA) Through Dialysis Synthetic Method PEA nanoparticles were prepared by dialysis synthetic method. Briefly, the copolymer (4 mg) was first dissolved in DMSO (2 mL). This solution was then added dropwise to 4 mL of PBS (pH 7.4, 10 mM, NaCl 100 mM) buffer or protein solution and stirred using a magnetic stirrer at 25° C. The resulting PEA nanoparticle suspension was extensively dialyzed against PBS (pH 7.4, 10 mM, NaCl 100 mM) for 24 h (MWCO 500 kDa), and the dialysis medium was changed five times. The amount of protein was determined by fluorescence measurements (FLS920, excitation at 492 nm). For determination of protein loading content, protein loaded NPs were dissolved in DMSO and analyzed with fluorescence spectroscopy, wherein calibration curve was obtained with protein/DMSO solutions with different protein concentrations.

Protein loading content (PLC) and protein loading efficiency (PLE) were calculated according to the following formulas:

PLC (wt. %)=(weight of loaded protein/total weight of loaded protein and polymer)×100%

PLE (%)=(weight of loaded protein/weight of protein in feed)×100%

The nanoparticles loaded FITC-BSA (bovine serum albumin) and FITC-CC (cytochrome C) have been prepared, table 6 and 7 represent the encapsulation results. The release of proteins from nanoparticles was investigated in the presence 10 mM DTT (FIG. 10+11). Remarkably, the more SS in the nanoparticles, the faster the protein was released. For example, 26, 39 and 80% of FITC-BSA was released in 44 h for PEA, PEA-SS (P2EG/Cys=88/12) and PEA-SS (P2EG/Cys=78/22) nanoparticles, respectively, moreover, almost 100% FITC-BSA was released in 12 h for PEA-SS (P2EG/Cys=57/43) nanoparticles.

TABLE 6

Encapsulation results FITC-BSA.

| nanoparticles | Protein-loaded nanoparticles | | |
|---|---|---|---|
| | Size (nm)/PDI | PLC (wt. %) | PLE (%) |
| PEA | 137/0.08 | 58 | 2.9 |
| PEA-SS(P2EG/Cys = 88/12) | 150/0.06 | 66 | 3.3 |
| PEA-SS(P2EG/Cys = 78/22) | 153/0.03 | 62 | 3.1 |
| PEA-SS(P2EG/Cys = 57/43) | 141/0.03 | 56 | 2.8 |

[a]FITC-BSA in feed was 5 wt. %.

TABLE 7

Encapsulation results FITC-CC.

| nanoparticles | Protein-loaded nanoparticles | | |
|---|---|---|---|
| | Size (nm)/PDI | PLC (wt. %) | PLE (%) |
| PEA | 130/0.08 | 55 | 2.8 |
| PEA-SS(P2EG/Cys = 88/12) | 145/0.08 | 68 | 3.4 |
| PEA-SS(P2EG/Cys = 78/22) | 147/0.06 | 65 | 3.3 |
| PEA-SS(P2EG/Cys = 57/43) | 132/0.07 | 60 | 3.0 |

[a]FITC-CC in feed was 5 wt. %.

TABLE 8

The results of loading DOX.

| Nanoparticles | DOX feed ratio (wt. %) | DOX loading content (wt. %) | DOX loading efficiency (%) | Size (nm)/PDI |
|---|---|---|---|---|
| PEA | 5 | 3.5 | 69.7 | 138/0.095 |
| | 10 | 6.5 | 65.2 | 144/0.08 |
| | 20 | 11.1 | 55.3 | 154/0.13 |
| PEA-SS (P2EG/Cys = 88/12) | 5 | 3.4 | 67.8 | 142/0.11 |
| | 10 | 6.4 | 63.8 | 146.5/0.10 |
| | 20 | 11.0 | 54.8 | 160/0.14 |
| PEA-SS (P2EG/Cys = 78/22) | 5 | 3.4 | 67.5 | 148/0.11 |
| | 10 | 6.1 | 61.2 | 150/0.14 |
| | 20 | 9.3 | 46.3 | 168/0.18 |
| PEA-SS (P2EG/Cys = 57/43) | 5 | 3.1 | 62.8 | 140/0.10 |
| | 10 | 5.6 | 56.4 | 145/0.12 |
| | 20 | 8.2 | 40.9 | 157/0.17 |

Example 10—In Vitro Release of Proteins

The release of FITC-BSA and FITC-CC from nanoparticles was investigated using a dialysis release method (MWCO 500 kDa) at 37° C. with 0.5 mL of protein-loaded nanoparticle suspensions against 30 mL PBS (pH 7.4, 10 mM, NaCl 100 mM) with 10 mM DTT. At desired time intervals, 6 mL release media was taken out and replenished with an equal volume of fresh media. The amounts of released proteins as well as proteins remaining in the dialysis tube were determined by fluorescence measurements (FLS920, excitation at 492 nm). The release experiments were conducted in triplicate and are represented in FIGS. 10+11.

Example 11—Preparation of DOX-Loaded Nanoparticles

DOX-loaded PEA or PEA-SS nanoparticles were also prepared by dialysis synthetic method. Briefly, the copolymer (4 mg) was first dissolved in DMSO (2 mL), then predetermined DOX solution was added it. This solution was then added dropwise to 4 mL of PBS (pH 7.4, 10 mM, NaCl 100 mM) buffer and stirred using a magnetic stirrer at 25° C. The resulting PEA or PEA-SS nanoparticle suspension was extensively dialyzed against PBS (pH 7.4, 10 mM, NaCl 100 mM) for 24 h (MWCO 3.5 kDa), and the dialysis medium was changed five times.

The amount of DOX was determined by fluorescence measurements (FLS920, excitation at 480 nm). For determination of DOX loading content, DOX-loaded NPs were dissolved in DMSO and analyzed with fluorescence spectroscopy, wherein calibration curve was obtained with DOX/DMSO solutions with different DOX concentrations.

Example 12—In Vitro DOX Release

In vitro release of DOX from the nanoparticles was studied using a dialysis tube (MWCO 12000, Spectrum) at 37° C. in PBS (pH 7.4, 10 mM, NaCl 100 mM) with or without 10 mM DTT. In order to acquire sink conditions, drug release studies were performed with 0.7 mL of micelle solution dialysis against 20 mL of the same medium. At desired time intervals, 6 mL release media was taken out and replenished with an equal volume of fresh media. The amount of DOX released was determined by using fluorescence (FLS920) measurement (excitation at 480 nm). The release experiments were conducted in triplicate. The results as presented in FIG. 12 are the average data.

Example 13—MTT Assays of PEA and PEA-SS Nanoparticles

HeLa cells were plated in a 96-cell plate ($5 \times 10^3$ cells/well) using 10% fetal bovine serum, 1% $_L$-glutamine, antibiotics penicillin (100 IU/mL) and streptomycin (100 µg/mL). After 24 h, prescribed amounts of PEA-SS/PEA nanoparticles were added and incubation for 48 h at 37° C. in an atmosphere containing % 5 $CO_2$. Then 10 µL of 3-(4,5-dimethylthiazol-2-yl)-2,5-diphenyltetrazoliumbromide (MTT) solution in PBS (5 mg/mL) was added and incubated for another 4 h. The medium was aspirated, the MTT-formazan generated by live cells was dissolved in 150 µL of DMSO for 20 min, and the absorbance at a wavelength of 490 nm of each well was measured using microplate reader (Bio-rad,ELX808IU). The cell viability (%) was determined by comparing the absorbance at 490 nm with control wells containing only cell culture medium. The experiments were performed four times each.

MTT assays showed that PEA-SS and PEA nanoparticles were practically nontoxic to Hela cells (cell viability >85%) up to a tested concentration of 2.4 mg/mL (FIG. 13).

Example 14—MTT Assays of DOX-Loaded PEA-SS/PEA Nanoparticles

Hela and MCF-7 cells were plated in a 96-well plate ($5\times10^3$ cells/well) using 10% fetal bovine serum, 1% $_L$-glutamine, antibiotics penicillin (100 IU/mL) and streptomycin (100 μg/mL). After 24 h, prescribed amounts of DOX-loaded PEA-SS/PEA nanoparticles (5 μg/mL, 10 μg/mL) were added and incubation for 48 h at 37° C. in an atmosphere containing 5% $CO_2$. Then 10 μL of 3-(4,5-dimethylthiazol-2-yl)-2,5-diphenyltetrazoliumbromide (MTT) solution in PBS (5 mg/mL) was added and incubated for another 4 h. The supernatant was carefully aspirated, and the MTT-formazan generated by live cells was dissolved in 150 μL of DMSO for 20 min. The absorbance at a wavelength of 490 nm of each well was measured using microplate reader (Bio-rad,ELX808IU). The cell viability (%) was determined by comparing the absorbance at 490 nm with control wells containing only cell culture medium. The experiments were performed four times each.

Figure 14B:
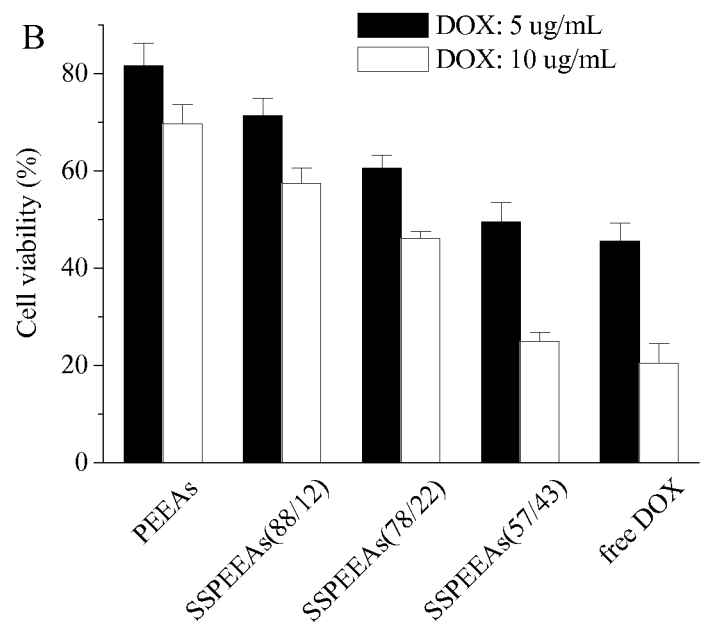

The cytotoxicity of DOX-loaded PEA-SS/PEA nanoparticles was investigated in Hela and MCF-7 cells using MTT assays. The cells were incubated with DOX-loaded nanoparticles for 48 h at drug dosages of 5 and 10 μg DOX equiv. $mL^{-1}$. Interestingly, there was an apparent dependency of anti-tumor activity on cystamine content, as well as DOX dosage (FIG. 14). For example, cell viability of 75.9, 69.7, 60.9 and 42.3% were observed for Hela cells treated for 48 h at a DOX dosage of 5 μg/mL and 69.3, 60.9, 45.1 and 20.7% at a DOX dosage of 10 μg/mL with DOX-loaded PEA, PEA-SS(P2EG/Cys=88/12), PEA-SS(P2EG/Cys=78/22) and PEA-SS(P2EG/Cys=57/43), respectively (FIG. 14A), indicating that the cytotoxicity of DOX-loaded nanoparticles intimately depends on disulfide content in the bioreducible environment. These results agree well with the in vitro as well as the intracellular DOX release profiles. In all cases, cell viabilities decreased with increasing drug dosages from 5 to 10 μg DOX equiv. $mT^{-1}$.

Example 13—Synthesis of Di-p-Toluenesulfonic Acid Salts of L-Arginine Ester

Di-p-toluenesulfonic acid salts of L-Arginine ester were prepared according to Scheme 3, Typically, L-Arginine (0.03 mol), p-toluenesulfonic acid monohydrate (0.06 mol), and Bis(2-hydroxyethyl) Disulfide (0.015 mol) in 60 mL toluene were placed in a flask equipped with a Dean-Stark apparatus, a CaCl2 drying tube and a magnetic stirrer. The solid-liquid reaction mixture was heated to reflux for 24 h until 1.65 mL (0.09 mol) of water was distilled. The reaction was cooled to room temperature. After the solvent was removed by rotary evaporation, the mixture was dried in vacuo overnight and finally purified by 3 times recrystallization in 2-propanol.

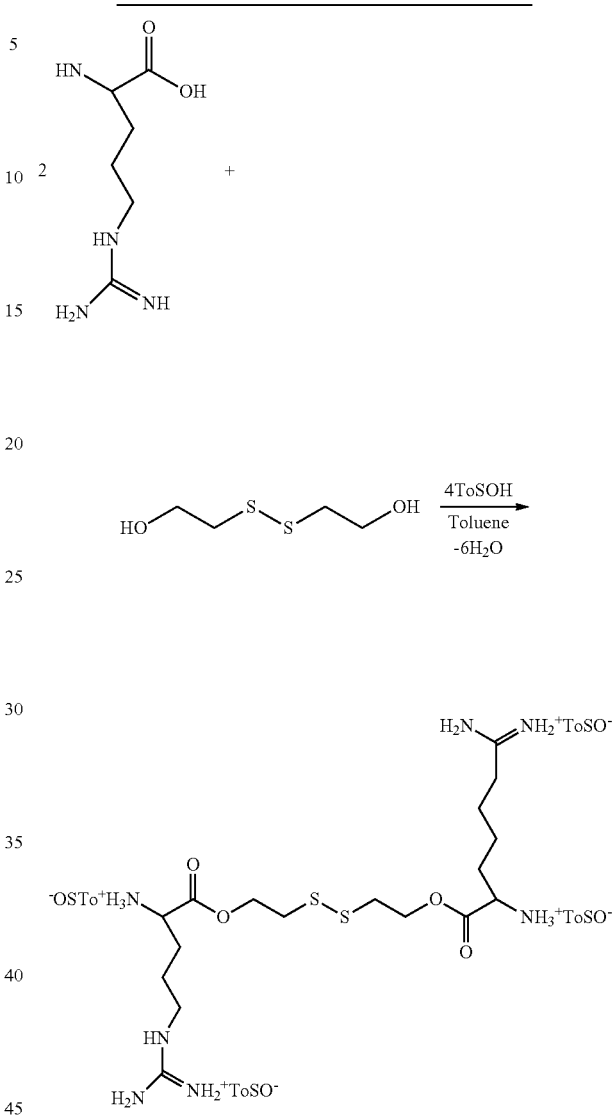

Scheme 6. Synthesis of di-p-toluenesulfonic acid salts of L-Arginine ester.

1H NMR (D2O, δ): 7.24-7.67 (16H, Ph-CH2-), 4.42 (4H, —C(O)OCH2CH2), 3.89 (4H, —NH—CH2-CH2-), 3.29 (4H, —NH—CH—), 2.76 (4H, —NH—CH2CH2SSCH2CH2-NH—), 2.56 (4.8H, Ph-CH3), 1.75-1.82 (8H, —CHCH2CH2CH2NH—).

Example 14—Synthesis of L-Arginine-4 Based Reduction-Sensitive Poly(Ester Amide)s Polymerization reactions were carried out in DMA at 70° C. with excess triethylamine for 48 h (Scheme 1). 1.1 equiv. of di-p-toluenesulfonic acid salts of di-p-nitrophenyl ester of dicarboxylic acid was combined with L-Arginine-4 ester and cystamine mixture (molar ratio: 80/20). After polymerization, the reaction mixture was purified by precipitation and subsequent Soxhlet extraction. Then, L-Arginine-4 based reduction-sensitive poly(ester amide)s were modified by 1.8 kDa PEI, as shown in Scheme 7. The un-reacted PEI was removed by dialysis (MW 3500).

Scheme 7: Synthesis routes to L-Arginine-4-based poly(ester amide)s 1H NMR Arg-4-SS(20%):1H NMR (D2O, δ): 7.15-7.64 (6.4 H, 1H NMR Arg-4-SS(20%):1H NMR (D2O, δ); 7.15-7.64 (6.4 H, Ph—CH2—), 4.01-4.12 (3.2 H, —C(O)—CH2CH2), 4.34 (1.6 H, —NH—CH—), 2.71, 3.29 (1.6 H, —NH—CH2CH2SSCH2CH2—NH—), 2.56 (4.8 H, Ph—CH3), 2.45 (8H, —C(O)—CHCH2CH2CH2C(O)—), 1.43-1.68(12.8 H, —C(O)—CH2—CH2—, —CH—CH2—CH2—, —C(O)—O—CH2—CH2—);

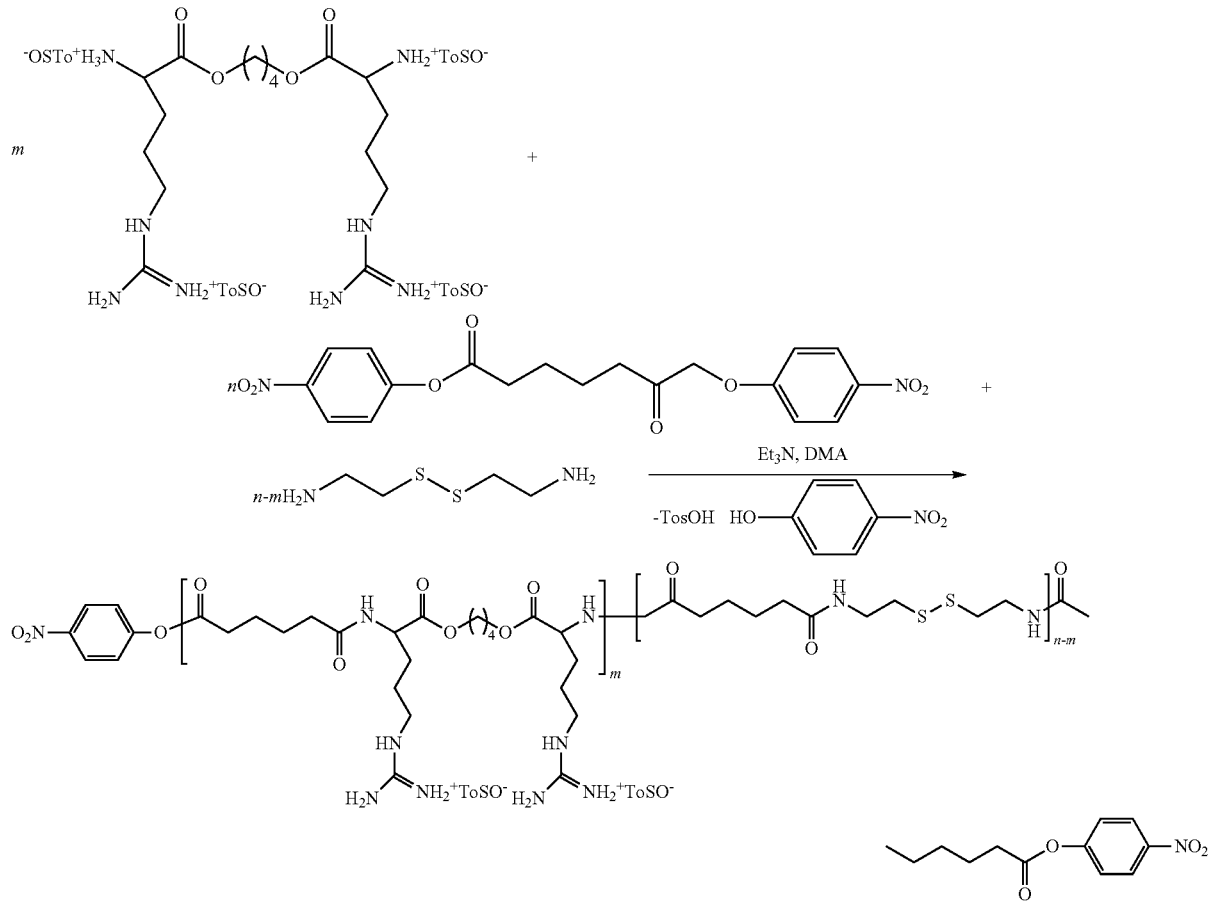

The invention claimed is:

1. A biodegradable polyesteramide comprising ester groups, amide groups, and disulphide linkages in the backbone of the PEA, wherein the polyesteramide is enzymatically degradable, wherein the polyesteramide comprise residues of alpha-amino acids, diols, aliphatic dicarboxylic acids, and optionally diamines, wherein at least one of the diols, aliphatic dicarboxylic acids, or diamines comprises a disulphide linkage.

2. The biodegradable polyesteramide according to claim 1, wherein the biodegradable polyesteramide has a Mw as measured by GPC in THF with polystyrene as standard of from 500 to 20,000 g/mol.

3. A biodegradable polyesteramide comprising a residue of at least one of the structural formulas I, II or III:

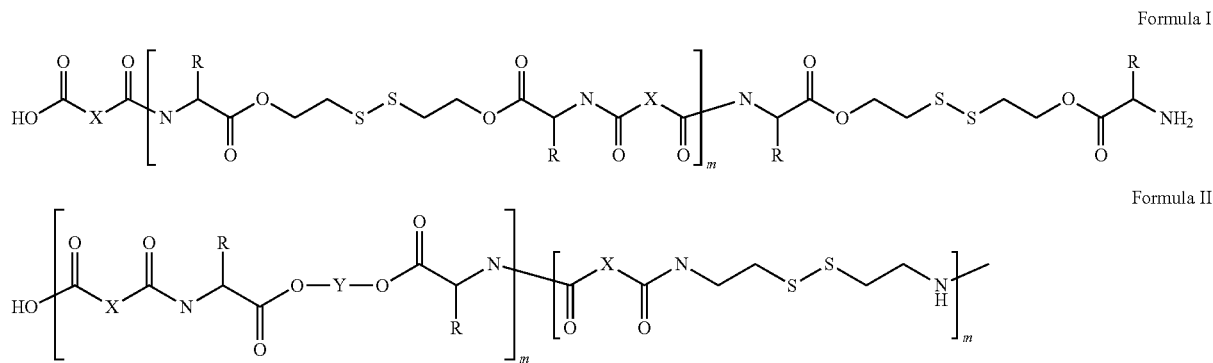

Formula III

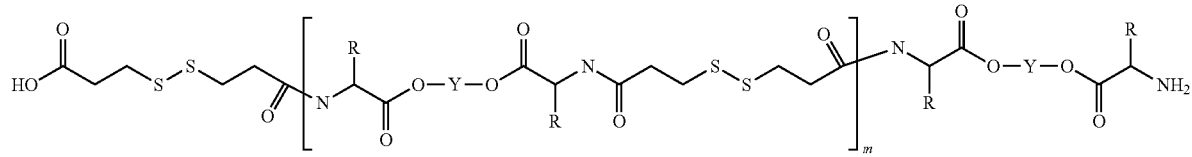

wherein m is from 5 to 300;
Y is a ($C_2$-$C_{20}$) aliphatic hydrocarbon or a ($C_2$-$C_{20}$) cycloaliphatic hydrocarbon;
X is independently an aliphatic hydrocarbon, a cycloaliphatic hydrocarbon, or an aromatic hydrocarbon; and
R is independently a side chain residue of an alpha amino acid with a positively charged group, a side chain residue of an amino acid with a negatively charged group, a side chain residue of an amino acid with an uncharged side group, or a side chain residue of an amino acid with a hydrophobic group.

4. The biodegradable polyesteramide according to claim 3 wherein the biodegradable polyesteramide comprises a residue of structural Formula I, wherein X is a ($C_2$-$C_{20}$) alkylene or ($C_2$-$C_{20}$) alkenylene and R is a side chain residue of phenylalanine.

5. The biodegradable polyesteramide according to claim 3 wherein the biodegradable polyesteramide comprises a residue of structural formula II, wherein X is ($C_2$-$C_{20}$) alkylene or ($C_2$-$C_{20}$) alkenylene, Y is ($C_2$-$C_{20}$)alkylene, ($C_2$-$C_{20}$) alkenylene, bicyclic-fragments of 1,4:3,6-dianhydrohexitols of structural Formula (IV), or combinations thereof, and R is a side chain residue of phenylalanine.

Formula IV

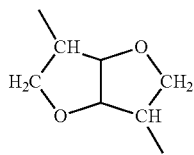

6. The biodegradable polyesteramide according to claim 3, wherein the biodegradable polyesteramide comprises a residue of structural formula III, wherein Y is ($C_2$-$C_{20}$) alkylene, ($C_2$-$C_{20}$)alkenylene, bicyclic-fragments of 1,4:3,6-dianhydrohexitols of structural Formula (IV), or combinations thereof, and R is a side chain residue of phenylalanine.

7. A drug delivery composition comprising the biodegradable polyesteramide according to claim 1 and a bioactive agent.

8. The drug delivery composition according to claim 7, wherein the bioactive agent comprises an anti-cancer agent.

9. A drug delivery system comprising microparticles or nanoparticles comprising the drug delivery composition according to claim 7.

10. A drug delivery system comprising microparticles or nanoparticles comprising the drug delivery composition according to claim 8.

11. A drug delivery system comprising microparticles, nanoparticles, micelles, liposomes, polymerosomes, microgels, nanogels, or nanotubes comprising the drug delivery composition according to claim 7.

12. The drug delivery system according to claim 9, wherein the drug delivery system comprises particles having an average diameter of from 1 to 40 μm.

13. The drug delivery system according to claim 9, wherein the drug delivery system comprises particles having an average diameter of from 20 nm to 800 nm.

14. A drug delivery composition comprising the biodegradable polyesteramide according to claim 3 and a bioactive agent.

15. The drug delivery composition according to claim 14, wherein the bioactive agent comprises an anti-cancer agent.

16. A drug delivery system comprising microparticles or nanoparticles comprising the drug delivery composition according to claim 14.

17. A drug delivery system comprising microparticles or nanoparticles comprising the drug delivery composition according to claim 15.

18. A drug delivery composition comprising the biodegradable polyesteramide according to claim 2 and a bioactive agent.

19. A drug delivery system comprising microparticles or nanoparticles comprising the drug delivery composition according to claim 18.

* * * * *